(12) United States Patent
Wu et al.

(10) Patent No.: US 12,193,868 B2
(45) Date of Patent: Jan. 14, 2025

(54) BREAST CALCIFICATION IMAGING PHANTOMS AND METHODS OF USE

(71) Applicant: The Board of Regents of the University of Oklahoma, Norman, OK (US)

(72) Inventors: Dee H. Wu, Edmond, OK (US); Elizabeth A. Jett, Edmond, OK (US); Natalie Stratemeier, Edmond, OK (US); Hong Liu, Norman, OK (US); Caroline J. Preskitt, Moore, OK (US); Weiyuan Wang, Edmond, OK (US); Min Yang, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 256 days.

(21) Appl. No.: 17/840,258

(22) Filed: Jun. 14, 2022

(65) Prior Publication Data
US 2022/0401057 A1 Dec. 22, 2022

Related U.S. Application Data

(60) Provisional application No. 63/211,321, filed on Jun. 16, 2021.

(51) Int. Cl.
*A61B 6/58* (2024.01)
*A61B 6/50* (2024.01)

(52) U.S. Cl.
CPC ............. *A61B 6/583* (2013.01); *A61B 6/502* (2013.01)

(58) Field of Classification Search
CPC ................................ A61B 6/583; A61B 6/502
See application file for complete search history.

(56) References Cited

U.S. PATENT DOCUMENTS 5,095,499 A * 3/1992 Wentz .................... A61B 6/583
378/207
6,285,740 B1 * 9/2001 Seely ....................... H05G 1/20
378/102

(Continued)

OTHER PUBLICATIONS

Abdurahman, Shiras, et al.; "Optimizing High Resolution Reconstruction in Digital Breast Tomosynthesis using Filtered Back Projection"; International Workshop on Digital Mammography; 2014; 8 pages.

(Continued)

*Primary Examiner* — Hugh Maupin
(74) *Attorney, Agent, or Firm* — Conley Rose, P.C.

(57) ABSTRACT

A radiographic phantom comprises: a body comprising a wax material or a wax-like material, wherein the body has an x-ray attenuation value that is approximately the same as that of a human tissue; and a plurality of crystalline test objects positioned on or within the body. A method comprises: obtaining a radiographic phantom comprising a body and a plurality of crystalline test objects positioned on or within the body, wherein the body comprises a wax material or a wax-like material, and wherein the body has an x-ray attenuation value that is approximately the same as that of a human breast tissue; performing an operation of the radiographic phantom and using a device; and assessing a performance of the device based on the operation.

20 Claims, 19 Drawing Sheets

(56) References Cited

U.S. PATENT DOCUMENTS

| | | | |
|---|---|---|---|
| 2006/0056580 A1* | 3/2006 | Frangioni | G01N 23/223 |
| | | | 378/207 |
| 2008/0075228 A1* | 3/2008 | Tasaki | A61B 6/542 |
| | | | 378/37 |
| 2010/0100092 A1* | 4/2010 | Turner | A61B 18/1815 |
| | | | 606/33 |
| 2010/0104505 A1 | 4/2010 | O'Connor | |
| 2013/0236513 A1* | 9/2013 | Guelcher | A61K 38/1875 |
| | | | 514/769 |
| 2014/0002106 A1 | 1/2014 | Lee et al. | |
| 2019/0388054 A1* | 12/2019 | Qiu | G09B 23/286 |
| 2021/0113146 A1 | 4/2021 | Pogue et al. | |
| 2021/0128098 A1 | 5/2021 | Niremberg | |
| 2021/0393220 A1 | 12/2021 | Boone et al. | |
| 2022/0082500 A1 | 3/2022 | Dacosta et al. | |
| 2023/0060834 A1* | 3/2023 | Sheng | A61B 6/032 |

OTHER PUBLICATIONS

Abdurahman, Shiras, et al.; "Out-of-Plane Artifact Reduction in Tomosynthesis Based on Regression Modeling and Outlier Detection"; International Workshop on Digital Mammography; 2012; 8 pages.

Breast Cancer Foundation NZ; "DCIS (Ductal Carcinoma in Situ)"; https://www.breastcancerfoundation.org.nz/breast-cancer/types-of-breast cancer/pre-invasive; 2017; 6 pages.

Horvat, Joao, V., et al.; "Calcifications at Digital Breast Tomosynthesis: Imaging Features and Biopsy Techniques"; RadioGraphics; vol. 39, No. 2; Jan. 25, 2019; 12 pages.

Newsshooter; "Canon's Dual Gain Output Sensor Explained"; https://www.newsshooter.com/2020/06/05/canons-dual-gain-output-sensor-explained/; Jun. 5, 2020; 5 pages.

O'Brien, Jane; "Ductal Carcinoma in Situ (DCIS)"; http://www.melbournebreastcancersurgery.com.au/wp-content/themes/ypotheme/pdf/ductal-carcinoma-in-situ-dcis.pdf; 2020; 17 pages.

Platisa, Ljiljana, et al.; "Channelized Hotelling Observers for the Assessment of Volumetric Imaging Data Sets"; Journal of the Optical Society of America; vol. 28, No. 6; Jun. 2011; 20 pages.

Radiology Key; "Mammographic Analysis of Breast Calcifications"; https://radiologykey.com/mammographic-analysis-of-breast-calcifications/; Dec. 24, 2015; 15 pages.

Smithuis, Robin, et al.; "Differential of Breast Calcifications" The Radiology Assistant; https://radiologyassistant.nl/breast/calcifications/differential-of-breast-calcifications; May 11, 2008; 29 pages.

Zonderland, Harmien, et al.; "Bi-RADS for Mammography and Ultrasound 2013"; The Radiology Assistant; https://radiologyassistant.nl/breast/bi-rads/bi-rads-for-mammography-and-ultrasound-2013; Oct. 8, 2014; 47 pages.

* cited by examiner

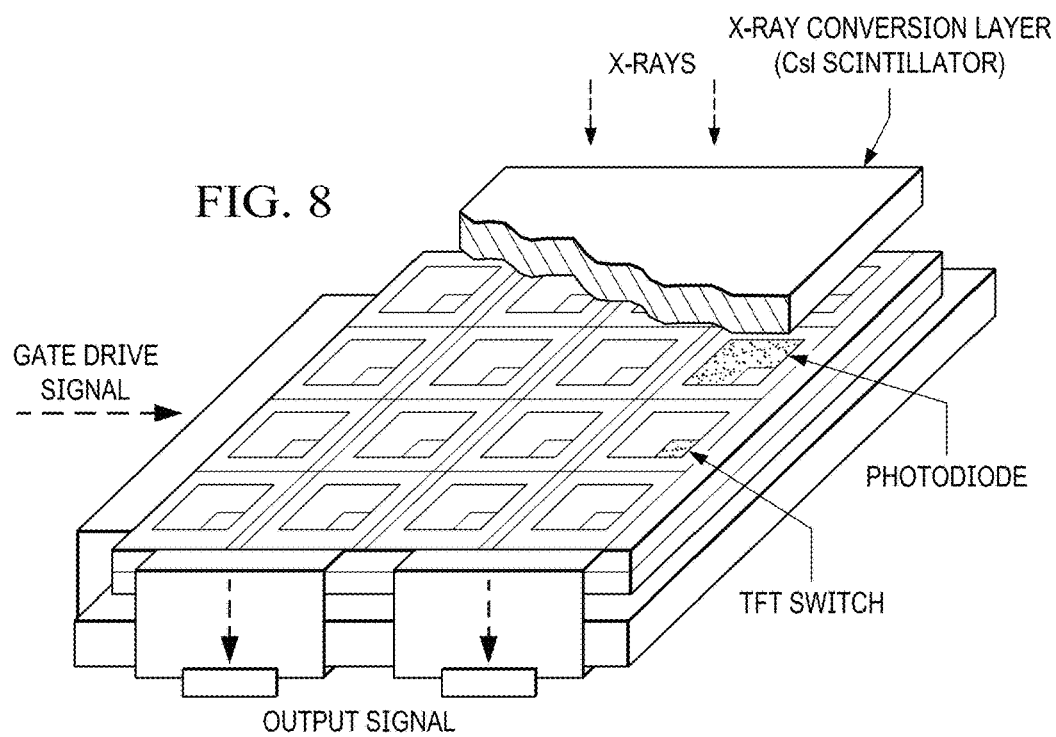
FIG. 8
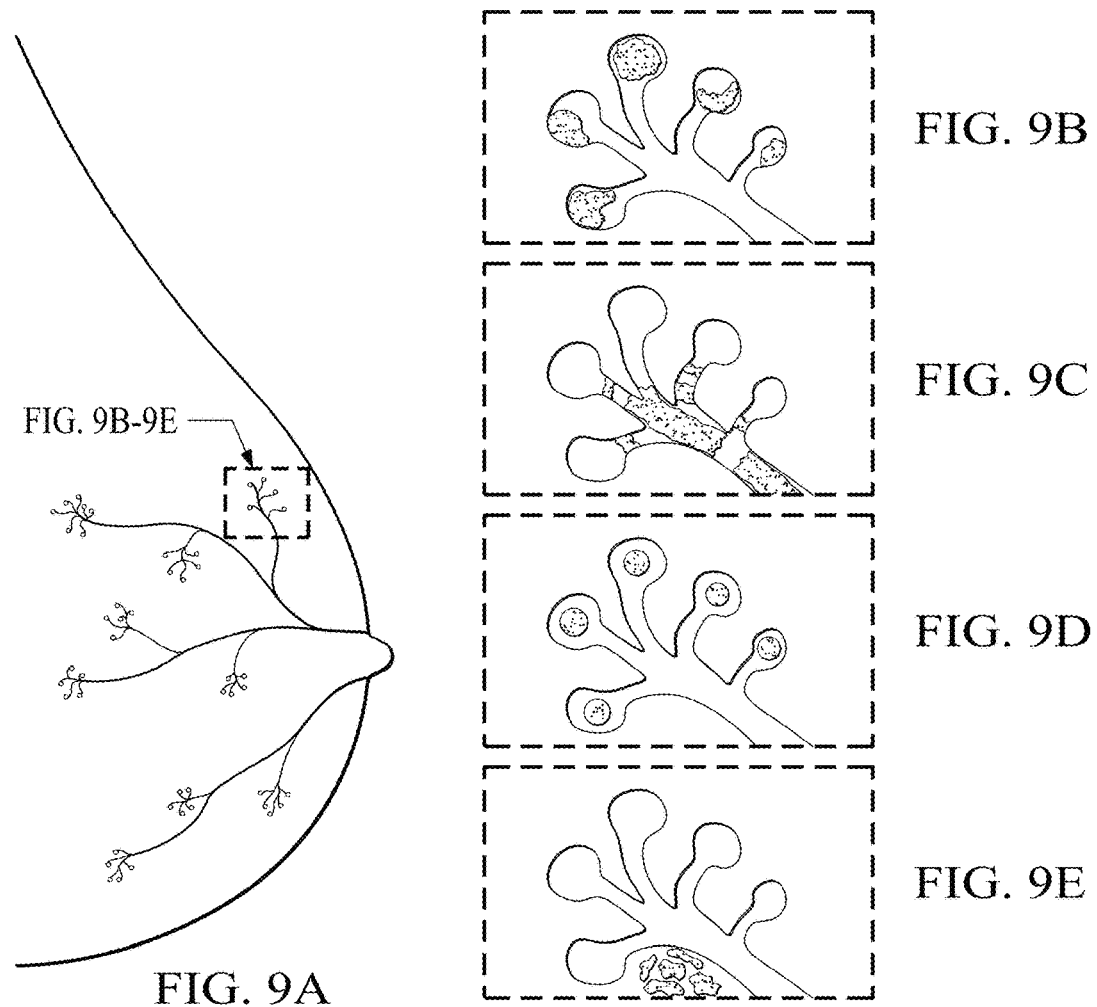
FIG. 9A
FIG. 9B
FIG. 9C
FIG. 9D
FIG. 9E

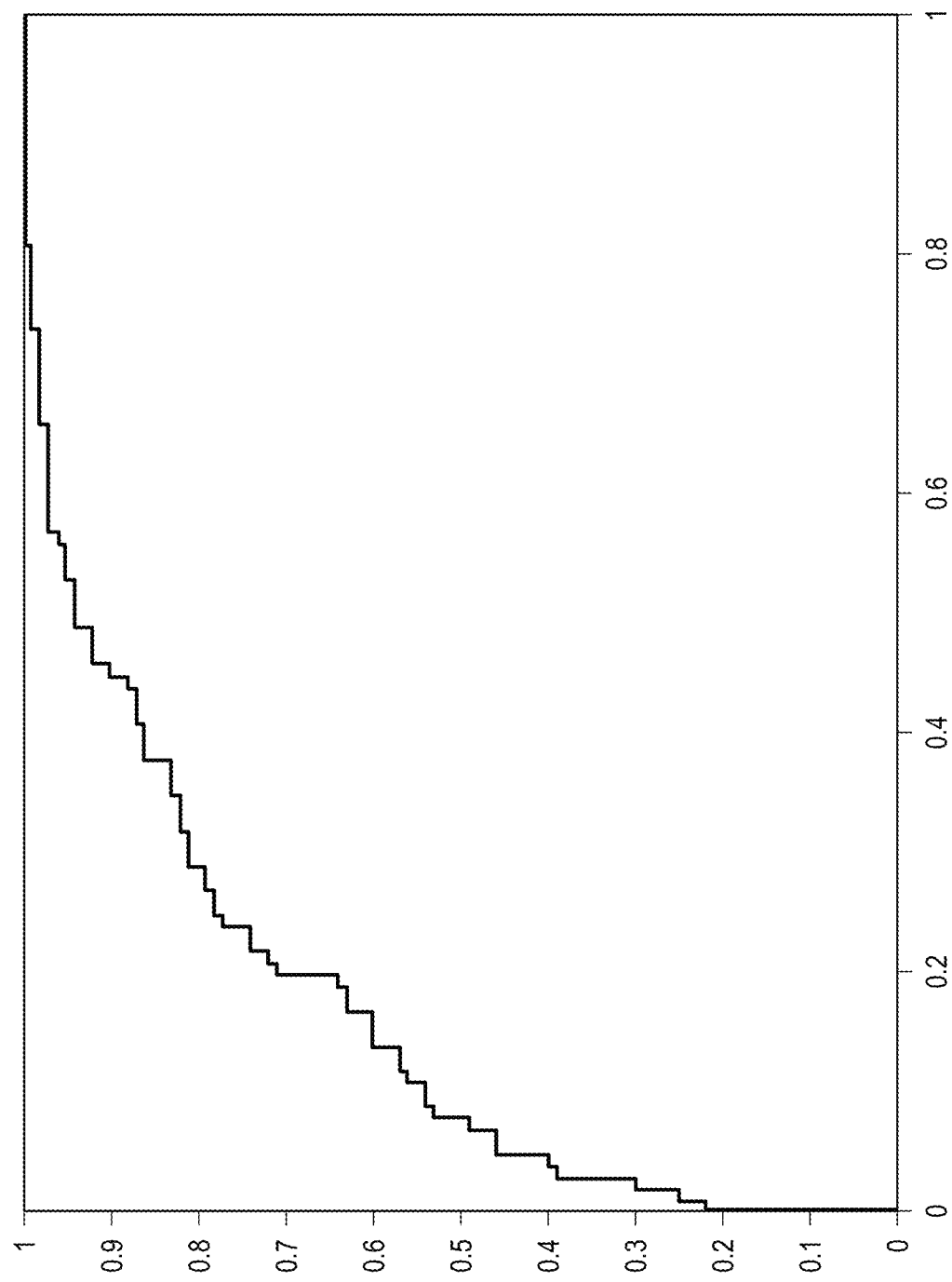

BREAST CALCIFICATION IMAGING PHANTOMS AND METHODS OF USE

CROSS-REFERENCE TO RELATED APPLICATIONS

This claims priority to U.S. Prov. Patent App. No. 63/211,321 filed on Jun. 16, 2021, which is incorporated by reference.

STATEMENT REGARDING FEDERALLY SPONSORED RESEARCH OR DEVELOPMENT

Not applicable.

BACKGROUND

Breast tissue calcifications are potentially one of the largest concerns for radiologists when they read mammographic, such as tomosynthesis, images. Breast phantoms are important for investigating and accurately assessing the performance of new mammography devices, algorithms, and systems, as well as for use as training tools. For example, phantoms can be used to facilitate the comparison between devices sold by vendors, for example in evaluating which angle to use during imaging. For example, tomosynthesis angles for various devices vary from a maximum of 15° to over 50°. However, many currently available phantoms lack equivalence to biological tissues. For example, various systems use 'swirled' epoxy, 'nylon' strings, and lead beads or BBs. These models do not satisfy or appear to be close to that necessary to gain confidence for the evaluation of calcifications. The materials do not have properties such as density and x-ray attenuation that are similar or equivalent to those in the body. Thus, such models lack the adequate realistic properties needed for acceptance testing. These models do not provide acceptable standards for the development of instruments and reconstruction algorithms, particularly for tomosynthesis. Improved phantom models are thus needed. Specifically, phantoms with constituent properties that more adequately model actual biological tissues and features such as calcifications are needed.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness.

FIG. 8 shows an image of a flat panel detector.

FIG. 9A is an image of a phantom with cavities, or artificial lobules, that mimic microscopic lobules of breast glands called lobes, which are the breast structures that produce breast milk. The artificial lobules can be constructed to have crystal patterns that mimic the calcification patterns of biological lobules. FIGS. 9B-9E are magnified, cross-section views of the lobules in FIG. 9A.

FIG. 12D is a graph showing an ROC analysis as performed by the computer evaluation. Background can be constructed with the lumpy pattern density.

DETAILED DESCRIPTION

Figure 1:
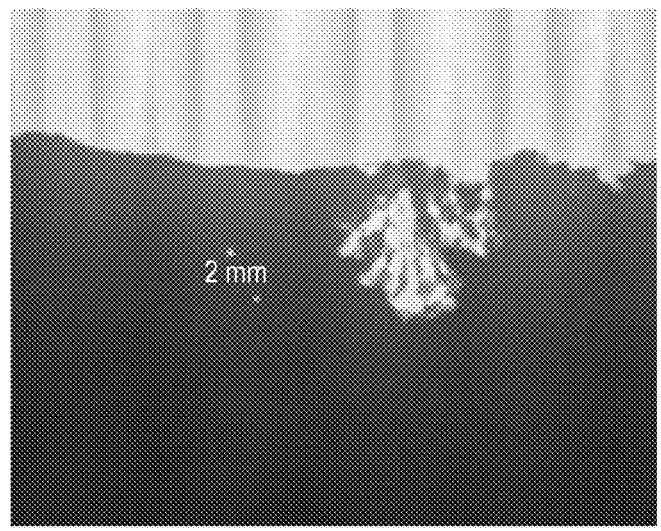
FIG. 1 is a tomosynthesis image of an NaCl crystal that was grown on dolomite rock, then transplanted into paraffin wax to model a breast calcification.
Figure 2:
FIG. 2 is a radiographic image showing a sample of hydroxyapatite, a common element of calcification in the body, that was injected onto and subsequently embedded into paraffin wax for modeling a different structure, composition, and size of breast calcification.
Figure 3:
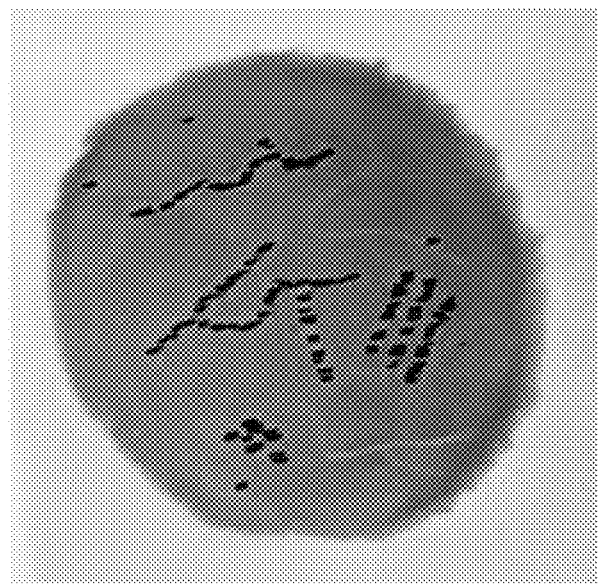
FIG. 3 is a tomographic image of a wax phantom of the present disclosure having NaCl crystals distributed within channels carved into the wax in various patterns. The NaCl crystals were formed by evaporating saltwater solution within channels.

The present disclosure is directed to a breast imaging phantom for the evaluation, comparison, and reliability of mammography, including but not limited to FFDM and tomosynthesis. In a non-limiting application, the phantom can be used to approximate and mimic the growth and sizes of crystals that develop within breast tissue and other body tissues by means of calcification.

In various non-limiting embodiments, the present disclosure is directed to: (a) creation of multiple patterns that mimic those of calcification patterns in breast cancer, (b) creation of crystal farms from which thresholds can be extracted to enable selection of patterns that reach an acceptable threshold of production, (c) use of wax or wax-like material in which crystals are embedded, wherein the waxy material mimics the composition of fatty and fibroglandular tissues of the breast, (d) imaging of the system in the presence of gel implants, (e) creation of channels for growing crystals, and (f) integration of a BI-RADS model for reporting findings.

In one embodiment, the present disclosure is directed to a phantom for image quality assessment for mammography, comprising crystalline objects or test objects that simulate tumors, lesions, calcifications and fibrillar extensions. The test objects may be configured in groups with random or non-random patterning. The test objects can be oriented in any direction and be various shapes and planes.

The following abbreviations apply:
AI: artificial intelligence
ASIC: application-specific integrated circuit
BI-RADS: Breast Imaging-Reporting and Data System
$CaCO_3$: calcium carbonate
$CaMg(CO_3)_2$: calcium magnesium carbonate, dolomite
cm: centimeter(s)
CHO: channelized Hotelling observer
CPU: central processing unit
DBT: digital breast tomosynthesis
DM: digital mammography
DQE: detective quantum efficiency
DSP: digital signal processor
EO: electrical-to-optical
ESF: edge spread function
FFDM: full-field digital mammography
FP: false positive
FPGA: field-programmable gate array
hydroxyapatite: hydroxy calcium phosphate
mm: millimeter(s)
MTF: modulation transfer function
NaCl: sodium chloride
NPS: noise power spectrum
OE: optical-to-electrical
PSF: point spread function
RAM: random-access memory
RF radio frequency
ROC: receiver operating characteristic
ROM: read-only memory
RX: receiver unit
SRAM: static RAM
TCAM: ternary content-addressable memory
TP: true positive
TX: transmitter unit
VICTRE: virtual imaging clinical trial for regulatory evaluation
3D: three-dimensional.

Before further describing various embodiments of the devices, compounds, compositions and methods of the present disclosure in more detail by way of exemplary description, examples, and results, it is to be understood that the devices, compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. Thus, while the devices, compounds, compositions, and methods of the present disclosure have been described in terms of particular embodiments, it will be apparent to those of skill in the art that variations may be applied to the devices, compounds, compositions and/or methods and in the steps or in the sequence of steps of the methods described herein without departing from the spirit, and scope of the inventive concepts described herein.

All patents, published patent applications, and non-patent publications mentioned in the specification or referenced in any portion of this application, including but not limited to U.S. Prov. Patent App. No. 63/211,321, are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular. Use of the word "we," "us," and/or "our" as a pronoun or modifier in the present disclosure refers generally to laboratory personnel, technicians, or other contributors who assisted in laboratory procedures and data collection and is not intended to represent an inventorship role by said laboratory personnel, technicians, or other contributors in any subject matter disclosed herein.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximate" or "approximately" are used to indicate that a value includes the inherent variation of error for the composition, the method used to administer the composition, or the variation that exists among the study subjects. As used herein the qualifiers "about" or "approximate" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The terms "about" or "approximate" or "approximately", where used herein when referring to a measurable value such as an amount, a temporal duration, an x-ray attenuation value, and the like, is meant to encompass, for example, variations of ±20%, or ±15%, or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 75% of the time, or at least 80% of the time, or at least 90% of the time, or at least 95% of the time, or at least 98% of the time.

Where used herein the term "similar" means having a resemblance of at least 20%, 15%, 10%, or 5% to a reference material. For example, in regard to tissue density, in a non-limiting embodiment, a material which is similar to a tissue has a density which differs from the tissue by no more than 20%, 15%, 10%, or 5%. For example, in regard to tissue x-ray attenuation, in a non-limiting embodiment, a material which is similar to a tissue has an x-ray attenuation which differs from the tissue by no more than 20%, 15%, 10%, or 5%. For example, in regard to breast tissue density, in a non-limiting embodiment, a material which is similar to a low-density fatty breast tissue has a density which differs from a density of low-density fatty breast tissue by no more than 20%, 15%, 10%, or 5%. A material which is similar to a dense breast tissue has a density which differs from a density of dense breast tissue by no more than 20%, 15%, 10%, or 5%. In regard to x-ray attenuation, in a non-limiting embodiment, a material which is similar to a low-density fatty breast tissue has an x-ray attenuation which differs from an x-ray attenuation of low density fatty breast tissue by no more than 20%, 15%, 10%, or 5%, and a material which is similar to a dense breast tissue has an x-ray attenuation which differs from an x-ray attenuation of dense breast tissue by no more than 20%, 15%, 10%, or 5%.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The compounds of the present disclosure may be combined with one or more pharmaceutically-acceptable excipients, including carriers, vehicles, diluents, and adjuvants which may improve solubility, deliverability, dispersion, stability, and/or conformational integrity of the compounds or conjugates thereof.

As used herein, "pure," "substantially pure," or "purified" means an object species (e.g., extracellular vesicles) is or are the predominant species present (i.e., on a molar basis it is more abundant than any other object species in the composition thereof), and particularly a substantially purified fraction is a composition wherein the object species (e.g., extracellular vesicles) comprises at least about 50 percent (on a molar basis) of all macromolecular species present. Generally, the object species (e.g., extracellular vesicles) in a substantially pure composition will comprise more than about 80% of all macromolecular species present in the composition, more particularly more than about 85%, more than about 90%, more than about 95%, or more than about 99%. The terms "pure," "substantially pure," or "purified" also refer to preparations where the object species (e.g., extracellular vesicles) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or at least 99.9% (w/w) pure, or at least 99.99% (w/w) pure.

Non-limiting examples of animals within the scope and meaning of this term include dogs, cats, rats, mice, guinea pigs, chinchillas, horses, goats, cattle, sheep, zoo animals, Old and New World monkeys, non-human primates, and humans.

In a non-limiting embodiment, the crystalline objects (test objects) in the phantom comprise $CaMg(CO_3)_2$ and/or hydroxyapatite. The test objects may also comprise calcium phosphate, calcium pyrophosphate, calcium sodium phosphate, calcium sodium pyrophosphate, calcium carbonate, calcium oxalate, calcium chloride, calcium oxide, sodium chloride, potassium chloride, barium chloride, potassium sulfate, sodium sulfide, aluminum oxide, or titanium oxide, and/or combinations of any of the above. The phantom models typically have a diameter in a range of about 6-8 cm and a depth in a range of about 2-6 cm or have a diameter in a range of about 12-15 cm and a depth in a range of about 1-3 cm. In a particular embodiment, the model has a diameter of about 7 cm and a depth of 3-5 cm. In another particular embodiment, the model has a diameter of about 14 cm and a depth of about 2 cm. The number, density, and positioning of the crystalline test objects vary depending on the model and can have multiple large test objects embedded, multiple small test objects embedded, or a mixture of both large and small test objects embedded. Patterns of test object can be arranged in clusters, linear tracks, curved tracks, or randomly dispersed, or in any manner known to persons of ordinary skill in the art. Crystallization is best suited when the environmental conditions for chemical equilibrium are around the central desired pKa of the primary salt that the crystal is made out of. This is typically best at ranges of +/−2 on the scale but each crystal solution will have its range of most useful working values. Temperature, pressure, and humidity can be controlled to preserve the products as well as assist the reaction of the processes.

The phantom may comprise a wax, a wax-like material, or a fatty-like material. Examples of waxes include, but are not limited to, animal waxes such as beeswax, sealing wax, Chinese wax, shellac wax, spermaceti wax, and lanolin wax. Examples of plant waxes include, but are not limited to, carnauba wax, soy wax, castor wax, tallow tree wax, bayberry wax, candelilla wax, esparto wax, Japan wax, jojoba oil, ouricury wax, and rice bran wax. In certain embodiments, the wax is an ester of ethylene glycol and two fatty acids.

The term "wax-like material" as used herein, refers, in at least certain embodiments, to a natural, semi-synthetic or synthetic material that is plastic (i.e., malleable) at normal ambient temperatures (i.e., 20-25° C.), has a melting point above 40° C., is very slightly soluble, practically insoluble, or insoluble in water (e.g., having a water-solubility lower than about 1:5000 (w/w)), and is composed of an ester of a fatty alcohol and saturated and unsaturated fatty acid(s), saturated and unsaturated fatty acid glyceride (mono-, di- or triglyceride), hydrogenated fat, hydrogenated vegetable oil, cholesterol, mineral waxes, hydrocarbons, petroleum-derived waxy materials, hydrophobic polymer having a hydrocarbon backbone, hydrophilic polymer having a hydrocarbon backbone, or a combination of one or more of the above-listed compounds.

Particular examples of such wax-like materials include, but are not limited to, petroleum-derived waxy materials such as paraffin waxes, microcrystalline wax, polyethylene waxes, Fischer-Tropsch waxes, chemically modified waxes (e.g., esterified or saponified waxes), substituted amide waxes, and polymerized alpha-olefins. Examples of hydrogenated vegetable oils include, but are not limited to, hydrogenated cottonseed oil, partially hydrogenated cottonseed oil, hydrogenated soybean oil, partially hydrogenated soybean oil, and stearyl alcohol. Examples of mineral waxes include, but are not limited to, ceresin waxes, montan wax extracted from lignite and brown coal, ozocerite, and peat waxes.

Combinations of the above-mentioned waxes or wax-like materials can also be used to construct the disclosed phantom.

The phantom model can be made to have the approximate density and x-ray attenuation factor of human breast tissues, ranging from that of fatty, low-density human breasts to that of high-density human breasts. The density of a breast depends on how much of the breast is composed of fatty tissue and how much is composed of fibroglandular tissue (milk glands, milk ducts, and supportive fibrous tissue). As the amount and distribution of the fibroglandular tissue increases, the amount of fatty tissue decreases, and the density of the breast increases, which increasingly inhibits (attenuates) the transmission of x-rays through the tissue. Where used herein, the density of a breast is classified according to the BI-RADS classification system. Category 1 includes breasts which are "almost entirely fatty" having a density of <25%. Category 2 includes breasts with "scattered fibroglandular densities," having a density in a range of 25%-50%. Category 3 includes breasts which are "heterogeneously dense," having a density in a range of 51%-75%. Category 4 includes breasts which are "extremely dense," having a density >75%. Breasts in categories 1 and 2 are generally referred to as "low-density," "non-dense," or "fatty." Breasts in categories 3 and 4 are generally referred to as "high-density" or "dense."

The phantom may comprise, in non-limiting embodiments, fibers or threads having a diameter in a range of from about 0.10 mm to about 1.0 mm, and a length in a range from 1 mm to 12 cm. In these embodiments, crystals can be grown on the fiber or thread and embedded within the body of the phantom.

Figure 14:
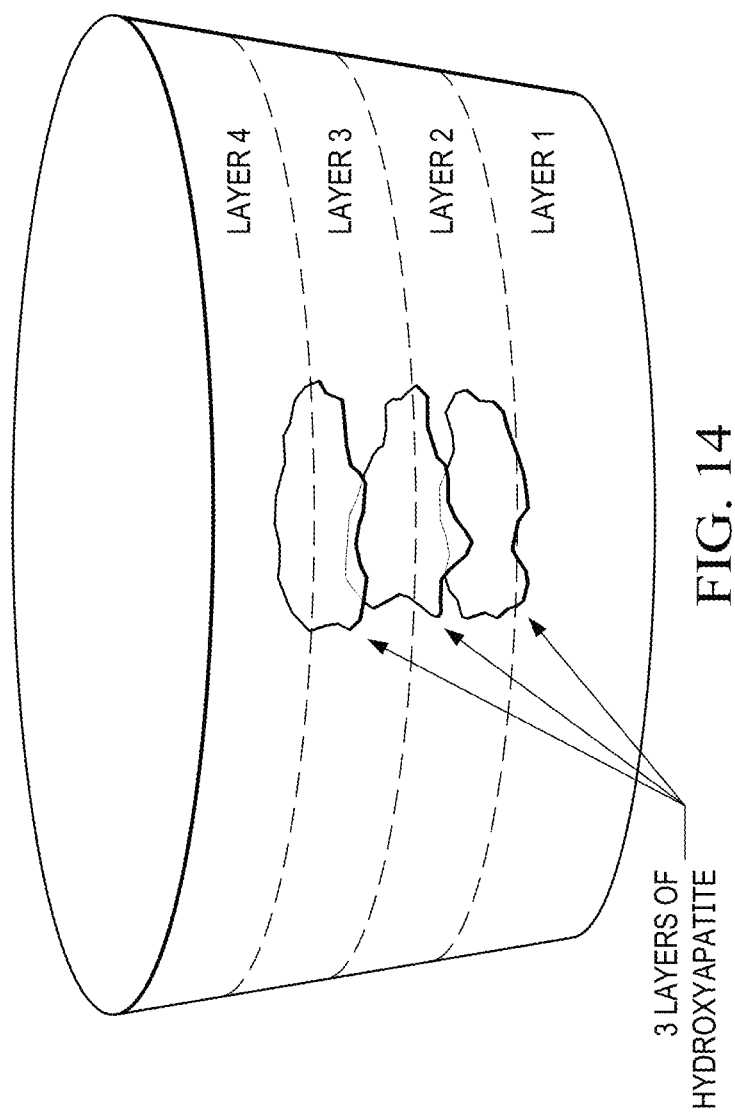
FIG. 14 shows a representation of hydroxyapatite layered in a wax phantom to create a large 3D calcification pattern.

In certain embodiments, the test objects of the phantom may have diameters in a range of from about 0.005 mm to about 1.0 mm, or in a range of from about 0.01 mm to about 0.5 mm, or more particularly in a range of from about 0.05 mm to about 0.35 mm. Particles may be disbursed throughout the phantom by evaporating a sodium and water solution or a calcium and water solution. Particles can also be placed by injecting hydroxyapatite cement. The size of the hydroxyapatite particles varies depending on the gauge of needle used to inject into the wax. Hydroxyapatite can be superimposed on multiple layers of the wax phantom in different patterns to form larger structures and shapes since it is an amorphous solid. One non-limiting example of hydroxyapatite layered into a multi-layered wax phantom is shown in FIG. 14.

In certain embodiments, the test objects in the phantom are positioned in patterns having the appearance of calcification patterns in breast tissue, including calcification patterns representative of those characteristic of breast cancer. For example, the test objects can be placed along linear or curved tracks carved within the waxy body to mimic vascularity. The inner diameter of these carved tracks can be, in non-limiting embodiments, between 0.1-1.5 mm depending on the gauge of needle, or other means, used to carve the tracks in the body. Even smaller (i.e., narrower) tracks can be made using microfluidic technology, such as lasers and very-thin-gauge needles to create the scoring, channels, and shapes. Additionally, calcification cluster patterns can be modeled by transplanting already-formed crystals onto the waxy body or creating layered hydroxyapatite crystal structures as mentioned above.

In addition to the types of crystalline materials mentioned above, the test objects of the present disclosure could comprise, in certain embodiments, salt crystals formed by evaporating an NaCl and water solution on the wax, or by evaporating a $CaCO_3$, NaCl, and water solution on the wax. Crystals can also be transplanted onto the wax after being grown on dolomite rock through the evaporation of vinegar. Calcium deposits can accumulate in the body and be indicative of a less medically concerning condition or a hallmark of more significant disease indicative of cancer. Hydroxyapatite crystals are particularly useful since they are a major component of bone and are representative of the various forms of materials that produce calcinosis in the body.

In certain embodiments, the phantoms may comprise additional biological and inorganic materials including but not limited to fibroblasts, sodium chloride, silica, potassium alum, chrome alum, monoammonium phosphate (ammonium phosphate), alum, magnesium sulfate (Epsom salt), and sugars.

In certain embodiments, a wax phantom body is made first, the wax phantom body is dried completely, and then crystals are placed onto the surface of the wax. The crystals can remain at the surface of the wax, or an additional layer or layers of wax can be added on top of the crystals to embed them.

In certain embodiments, the phantom comprises at least a first plurality of spaced-apart test objects positioned in a first plane in the body. The phantom may further comprise a second plurality of spaced-apart test objects positioned in a second plane. The planes may be both vertical, both horizontal, or orthogonal to each other at an angle between zero and 90°.

System Calibration

For calibration, most systems use flat-panel detectors (See FIG. 8). These panels, however can experience calibration issues such as lag. A detector has various properties including afterglow and speed of the detector. Faster detectors and lower afterglow come with cost effects. However, they affect the quality of the output.

Setting appropriate pixel size when calibrating the system is also necessary. Detectors have varying performance standards, whether they are high resolution or low resolution. Higher resolution entails more cost, so the tradeoff between obtaining target resolution and minimizing cost can be explored using the presently disclosed phantoms. Similarly, contrast resolution can be explored in calibrating system sensitivity range. A designer would have to target and specify the tradeoff of the machine. Using the presently disclosed phantoms will help to do this more appropriately and with more confidence.

Because flat-panel detectors have thousands of pixels, pixels may not always be uniform in signal. The phantoms disclosed herein can assist in the normalization of detectors in which pixels are uniform and gain of signal can be controlled. Gain is the range that the detector is amplified to and the range of sensitivity. Since the phantom has a known and uniform composition, it can be used to check against each pixel's signal. A designer would have to target and specify the tradeoff of the machine. The presently disclosed targets will help them do this more appropriately and with more confidence.

Tomosynthesis involves acquiring multiple projections at different angles in the x, y, or z direction, thus making the system very sensitive to geometric alignment. Geometric calibration can be done using the presently disclosed phantoms to correct for angles, thereby ensuring that the same angles are being used (standardized) across multiple systems. This is done by starting with a BB (a BB and the presently disclosed phantom can be used in conjunction), then measuring the source to the isocenter and source to the detector. Calibration is based on where the projections show the BB, for example in the center of the rotation, but calcification can also be used for fine tuning because it provides high spatial resolution of an important contrast. In tomosynthesis, a limited number of projections are acquired at various angles around the object. Therefore, the data acquired must be reconstructed. Out-of-plane signal artifacts can cause blur and impact quality of reconstruction. Small features, such as microcalcifications, can become blurred due to these artifacts, and their resulting reconstruction can be impacted by interpolation.

The presently disclosed phantoms can assist with reconstruction algorithm setup and calibration. One method of reconstruction that can be calibrated includes statistical outlier projections with high values (e.g., Grubbs's test, Chauvenet's criterion, and Box-Pierce test could be methodology for outlier evaluation). For example, one can use a statistical outlier projection method and a model-based regression to fit data for the 'outlier' training (using population-based parameters and standard deviation modeling). Filtering of breast tomosynthesis consists of MTF inversion, spectral, and slice thickness filtering. Linear combinations of the aforementioned filtering can be used. Note that MTF inversion filtering starts with a series of different order weighted basis functions (with different control parameters like cutoff frequency), and these weights can be set by tuning against the presently disclosed phantoms.

In super resolution, one way of providing the interpolated result is a coefficient combination of the maximum value or ordinal statistics evaluation (like a trimmed estimation of the maximum value). A trimmed estimator is an estimator derived by excluding some of the extreme values by a method sometimes known as "truncation." The goal is to get a more robust statistical estimate where the extreme values are considered to be outliers and are lowered in weight or not used in the value of the final trimmed estimator (for example a mean which is a sum of values, can either down-weight the contribution of the identified 'outliers' or exclude them entirely).

Further tuning of the final result is continued by iterative filtering in the image domain in which the local gradient in slab image is minimized to preserve local edges and microcalcifications. By using a known 'calcification phantom,' the parameters used in the reconstruction (such as weighting factors, thresholds, spatial filters, frequency parameters, phase, etc.) can be tuned.

Outside of the tomosynthesis system, the computer on which the reconstructed images are viewed must also be calibrated and sensitive to minute changes or differences in calcifications. This calibration can be done through a fixed method or a variable gain method. The former involves calibrating the slope of a flood field from one dark point to one light point, while the latter involves determining a line of best fit (linear or polynomial s-curve) between multiple points of varying darkness/brightness.

Crystal Farms

Figure 4:
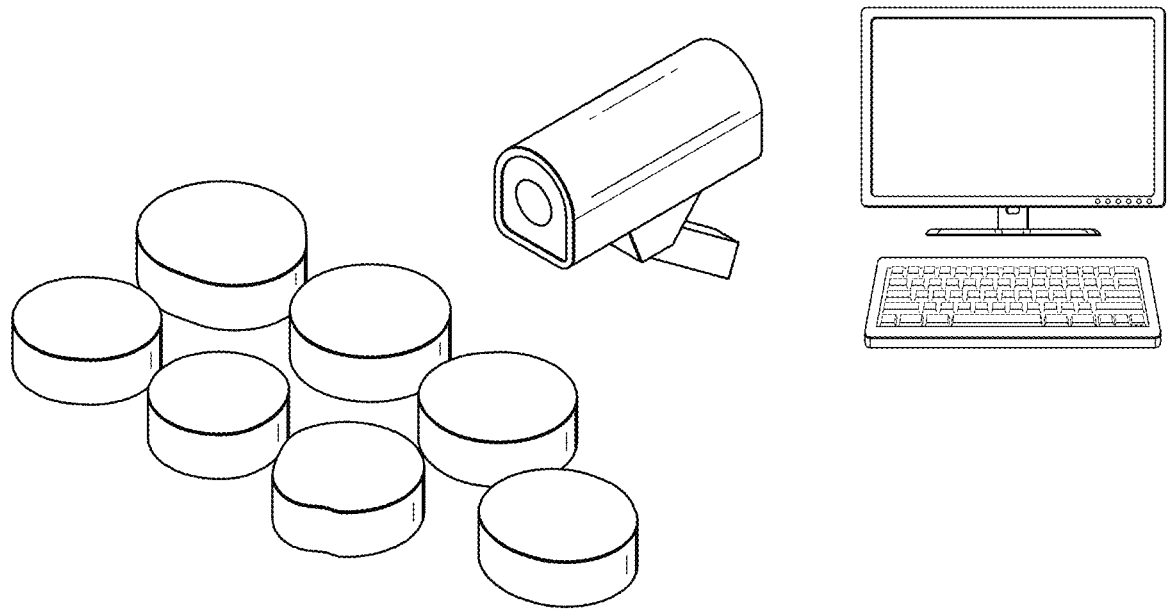
FIG. 4 shows a set of wax phantoms partitioned into various sizes and types. A camera mounted on an XYZ scaffold can be moved in three dimensions to select different phantoms having varying composition and techniques of insertion of test objects, depending on the radiographic image desired. The camera and a corresponding AI system (represented by the monitor image) can use image matching technology to compare particular calcification patterns to phantoms which are most similar in farm.
Figure 5:
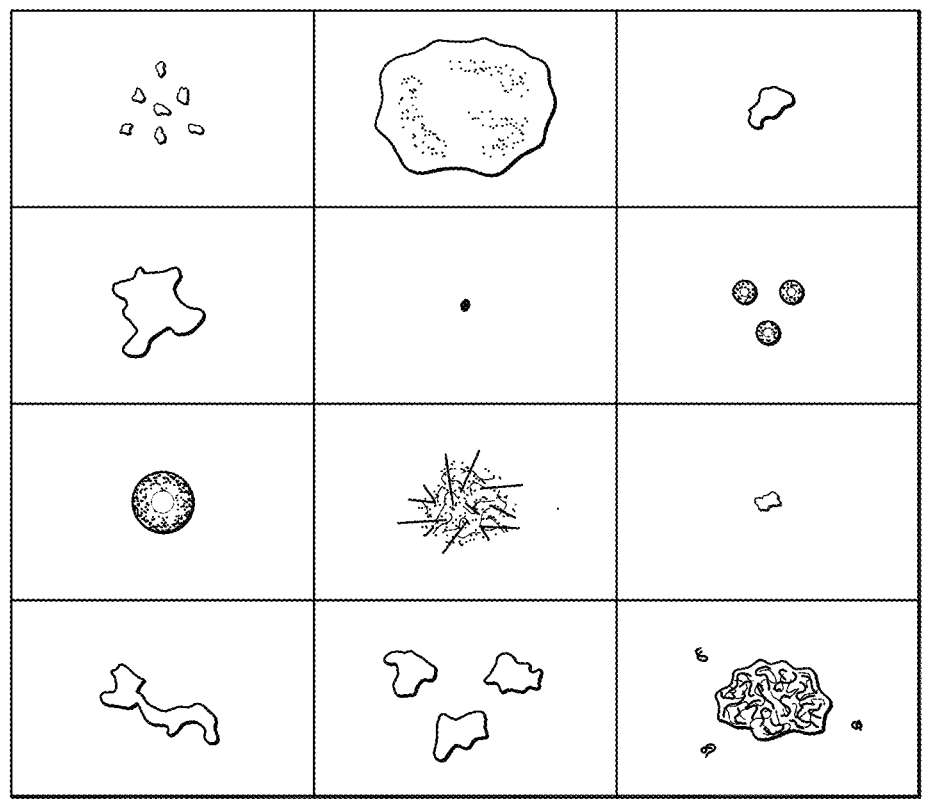
FIG. 5 is a representation of a "crystal farm" comprising various sizes and shapes of crystals on a surface medium. A camera can move around the planes of the farm to identify various shapes, types, and sizes of crystals to be selected for insertion into a wax phantom, depending on the patterns, shapes, sizes, etc., desired for a particular phantom. The camera and corresponding AI system uses image matching technology to compare desired calcification patterns from BI-RADS standards of reference to the calcification crystals present in the crystal farm.

Different types of crystal farms can be used to construct the presently disclosed phantoms. One non-limiting embodiment uses crystals (also referred to herein as "test objects") which have been grown in individual compartments on a medium (e.g., see FIG. 5). For example, these crystals can be NaCl crystals grown from evaporating saltwater, hydroxyapatite crystals injected onto the medium, or dolomite crystals grown from evaporating vinegar. The goal is to create a farm of crystals with varying sizes, shapes, and characteristics, which can be selected and then implanted into the wax phantom. In another embodiment, the phantoms themselves can be arranged in an array (a phantom farm). The phantoms already have embedded in them various compositions and configurations of test objects (e.g., see FIG. 4). Depending on the model needed for imaging or calibration, the desired phantom can be selected from the farm array (discussed below).

Robotics

The methods of construction or use of the phantoms of the present disclosure can employ use of robotics. For example, in one non-limiting embodiment, a robotic arm with a digital camera at the end is connected to a computer and corresponding AI system as discussed below. The robotic arm and camera move in linear sections over the phantom farm or crystal farm (e.g., see FIGS. 4 and 5). Based on feedback from the AI system, the arm moves to find the desired crystal structure, pattern, or phantom model. A secondary robotic arm or robotic system can be used to excavate the selected crystal structure or phantom from the farm. In cases of excavating the crystal, the robotic arm can transplant the crystal onto the wax phantom. Depending on the robotic system used, these crystals can be on a microscopic or macroscopic level.

AI

An AI system can be used in conjunction with the robotic system. The AI system receives image input from the camera and uses image matching/comparison technology to select a crystal that is most similar to the calcification needing to be modeled. Similarly, it can select an already constructed phantom that is most similar to the model desired. AI uses neural networks and is very helpful in the evaluation of image object recognition and detection. Common methods include but are not limited to Tensorflow and pyTorch. It can also be improved with transfer learning, etc. AI can be used for detection and correction of parameters for image reconstruction and validation of samples in the 'farm.'

Microfluidics

Microfluidic technology involves manipulating fluid on a microscopic or sub-millimeter level. Microfluidics can be used to model microscopic calcification in the presently disclosed phantoms. Calcifications can be formed by evaporating NaCl solution from microscopic channels. Microfluidics can also be employed to create a mold for microscopic hydroxyapatite crystals. Since any pattern of channel can be created using microfluidic technology, the phantom can also model specific patterns such as partial filling of vascular ducts and cavities with crystals or calcifications or specific vascular structures which calcify. In a non-limiting example, FIG. 9B shows amorphous, heterogenous calcifications; FIG. 9C shows fine, linear, inter-ductal calcifications that are likely malignant; FIG. 9D shows smooth, lucent, centered, homogenous calcifications that are characteristic of milk calcium and that are likely benign; and FIG. 9E shows stromal calcifications that are characteristic of dystrophic calcification caused by trauma and that are likely benign.

Synthetic Images

Figure 6A:
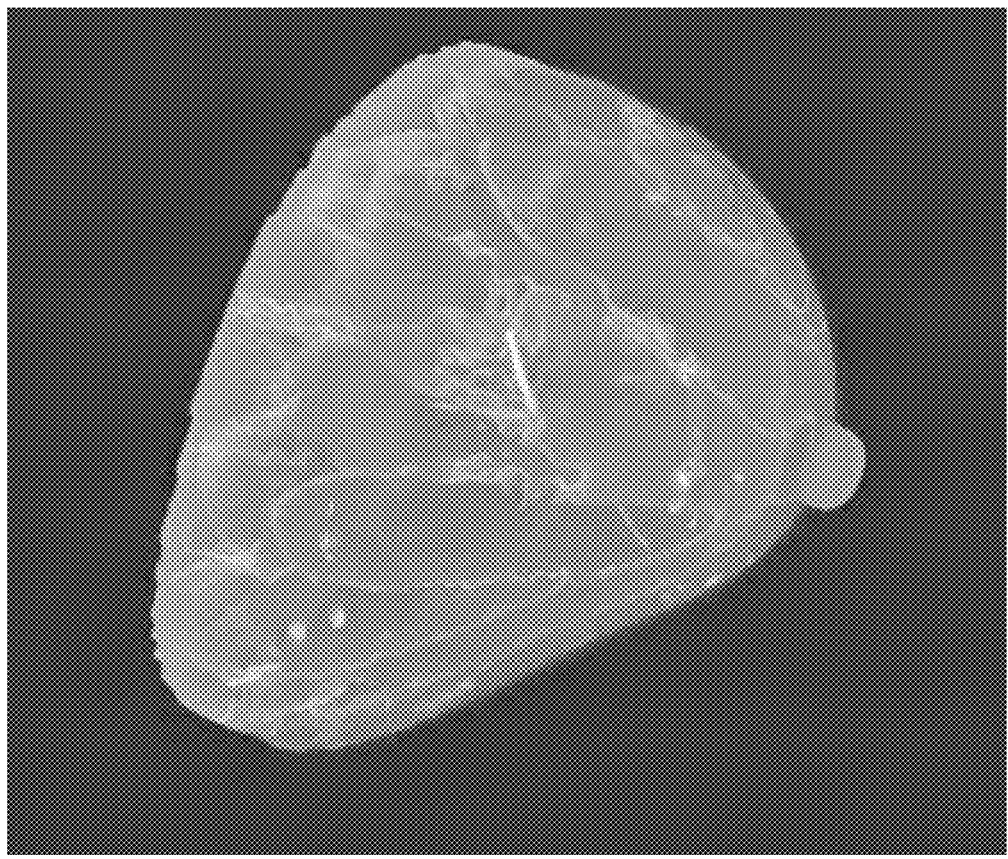
FIG. 6A is a synthetic image of a mathematically-constructed 3D breast model. Properties and behavior are known since the model is structured using mathematics and can be easily replicated and modified. The synthetic images can be created physically (e.g., by 3D printing and/or machining) using synthetic (digital) designs with targeted behaviors (e.g., resolution, and system metrics) and used as a test set.
Figure 6B:
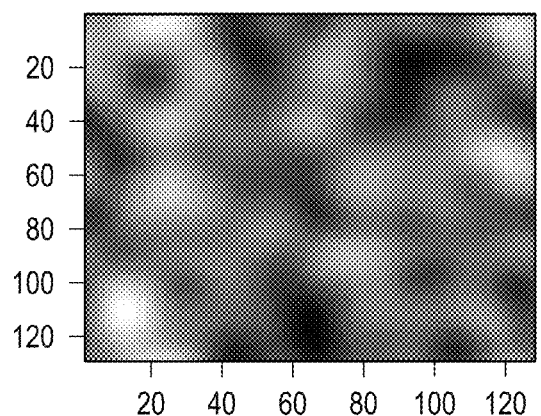
FIG. 6B shows sections through the breast model of FIG. 6A that are created mathematically.
Figure 6B:
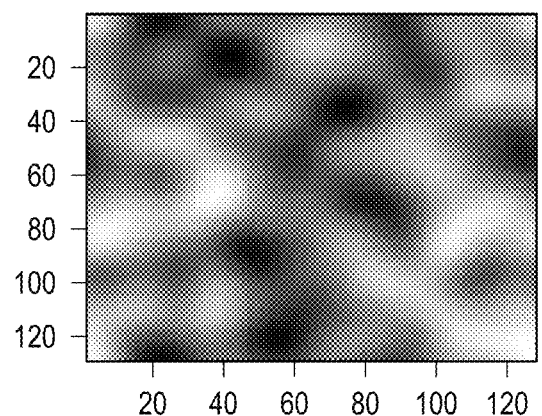
Figure 6B:
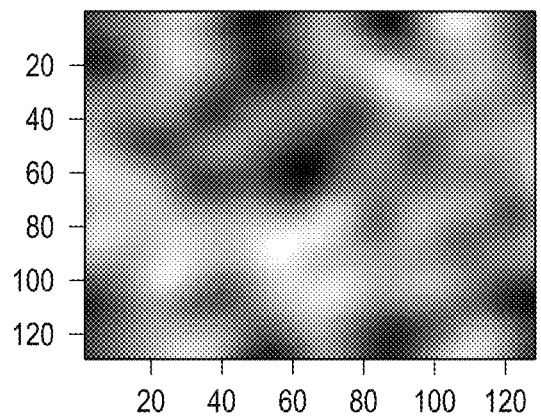
Figure 6B:
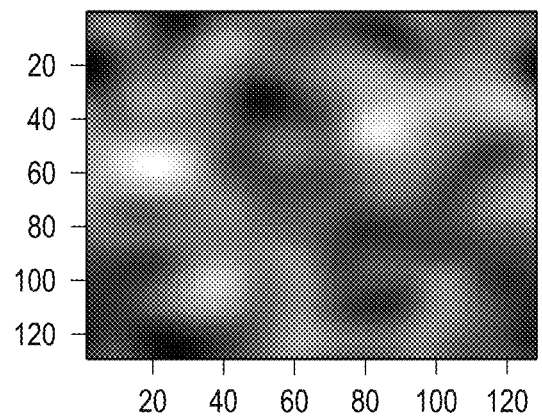
Figure 7:
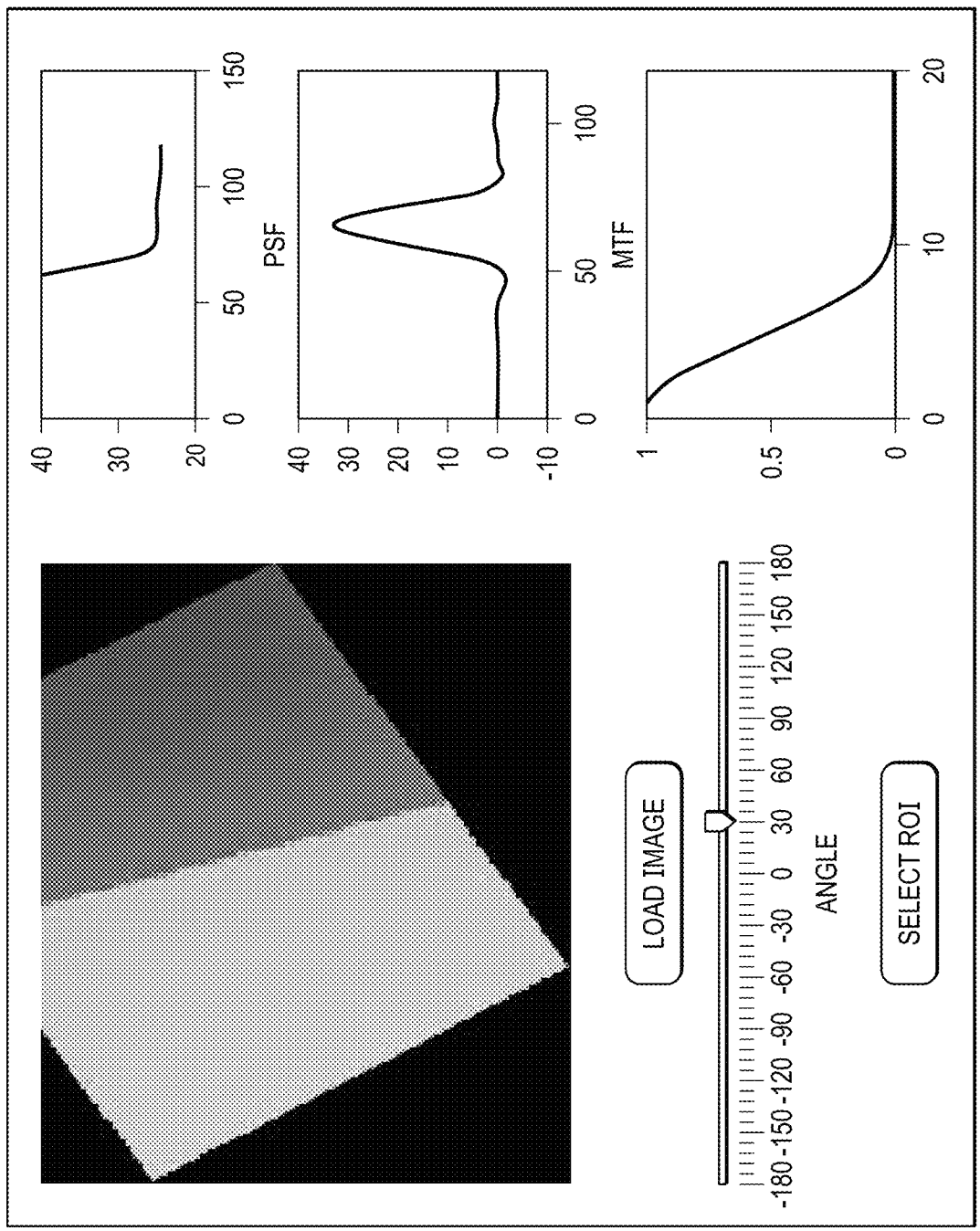
FIG. 7 shows metrics of system performance analyzed by software. PSF is a measure of resolution properties of an imaging system. ESF measures spatial distribution of low-amplitude phenomenon, such as glare or scatter along the edge of the field of view. MTF is the accepted standard for characterization of spatial resolution and shows which areas of an image are passing in terms of signal (>threshold) and which areas are not (<threshold). NPS and DQE implementations were also used for evaluation. These measures describe system performance of a machine and test signal quality. Dual gain output sensors could also be used. With such sensors, one sensor has a saturation-priority gain and another sensor has a noise-priority gain. Each sensor provides its own image, and the two sensors are fused.
Figure 10A:
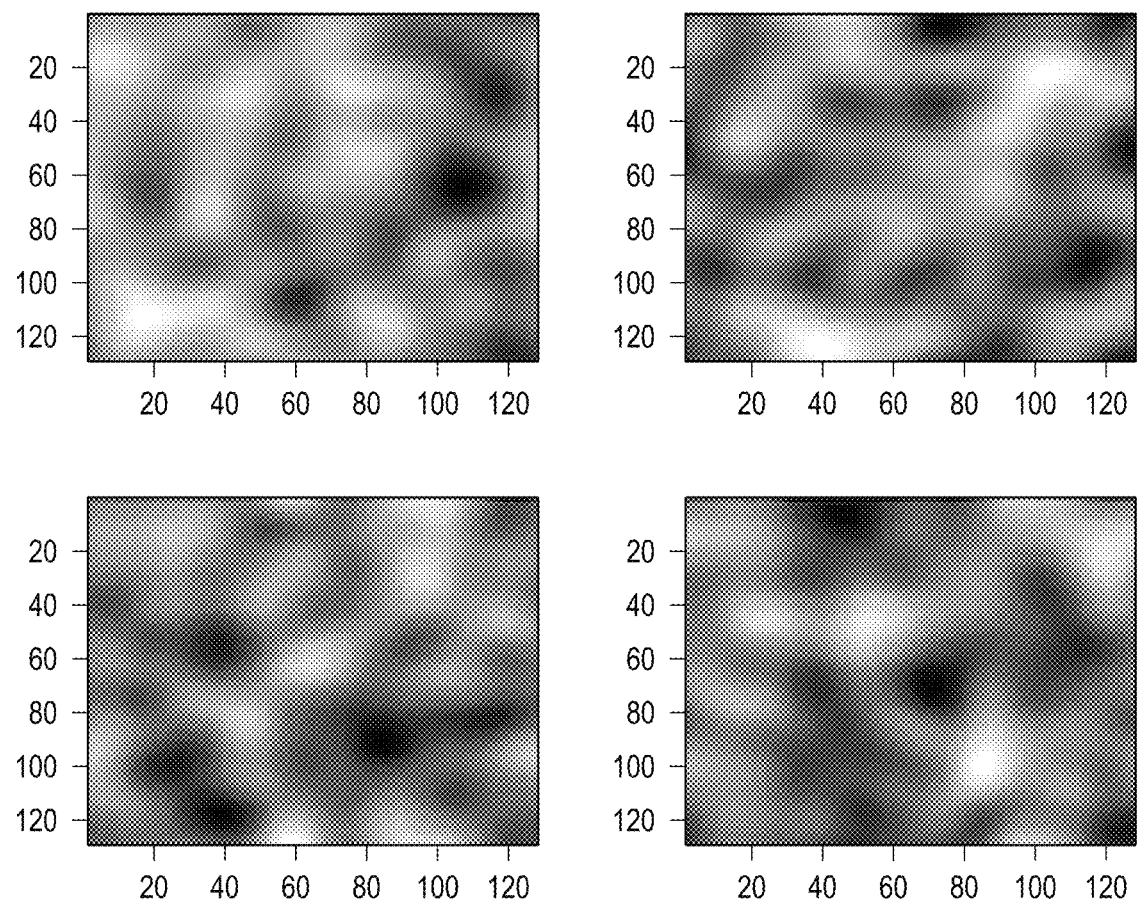
FIG. 10A shows synthetically created lumpy background noise textures.
Figure 10B:
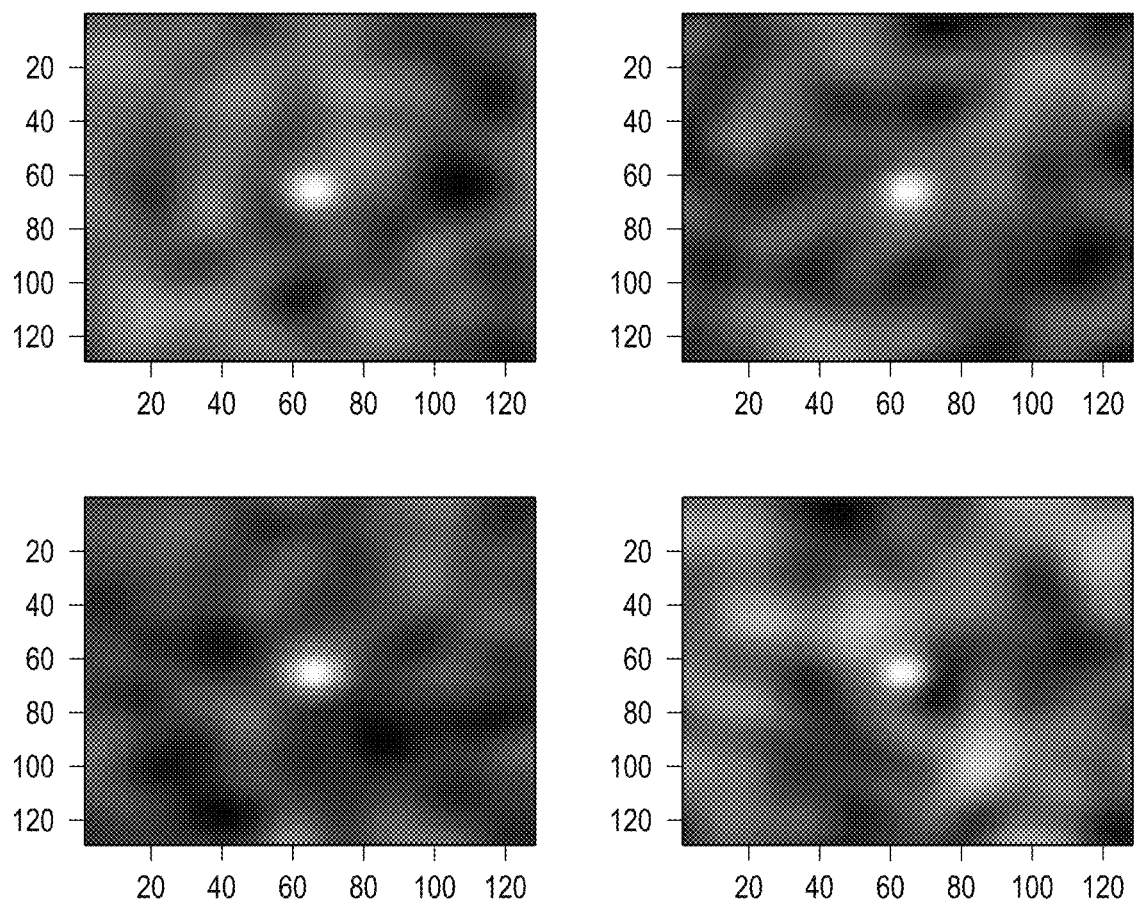
FIG. 10B shows the synthetically created lumpy backgrounds of FIG. 10A with signals buried under the noise textures.
Figure 10C:
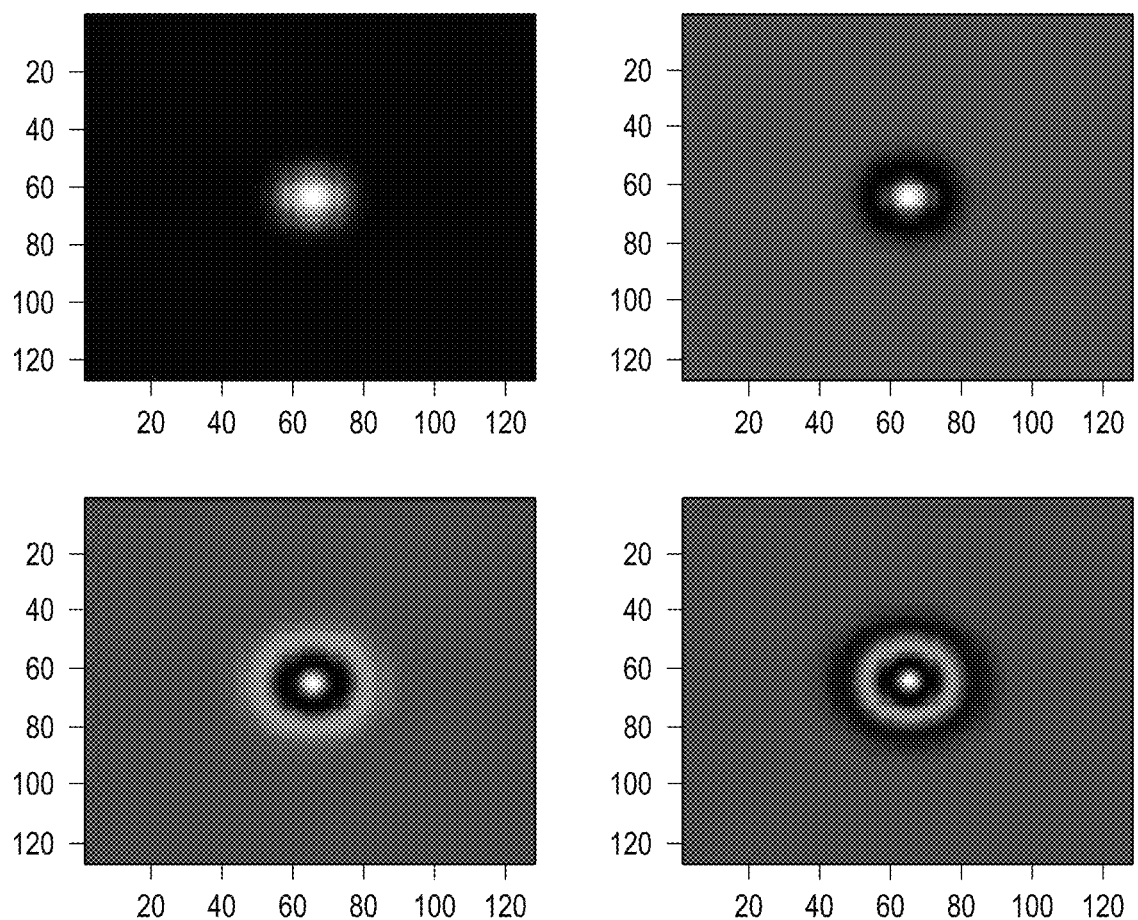
FIG. 10C shows examples of a Laguerre basis function, which is a mathematical transform, for CHO analysis for mimicking eye behavior.
Figure 11A:
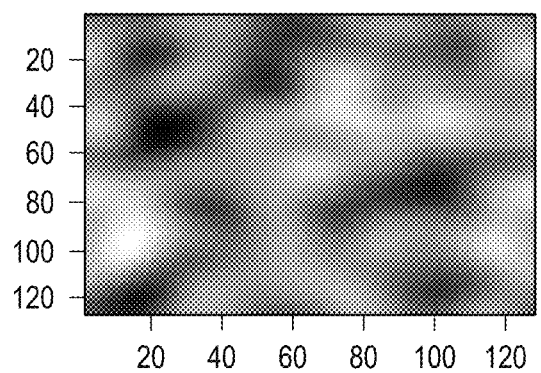
FIG. 11A shows a synthetically-generated lumpy background.
Figure 11A:
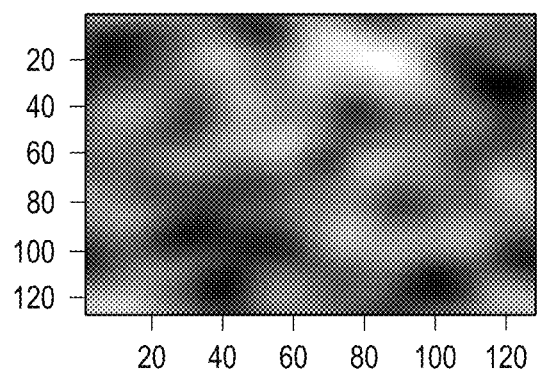
Figure 11A:
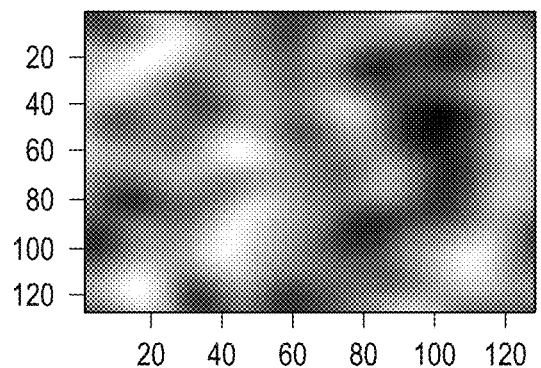
Figure 11A:
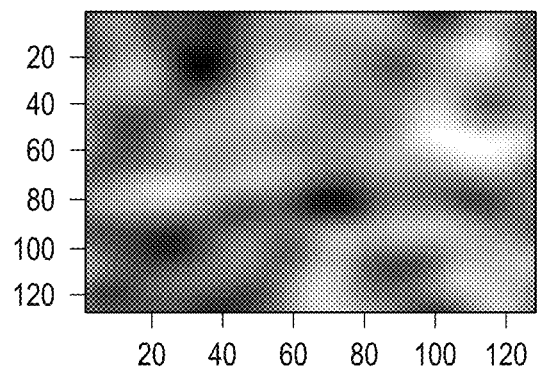
Figure 11B:
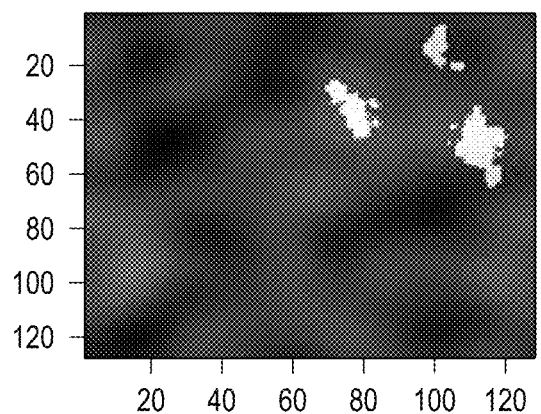
FIG. 11B shows calcifications superimposed upon the lumpy background of FIG. 11A.
Figure 11B:
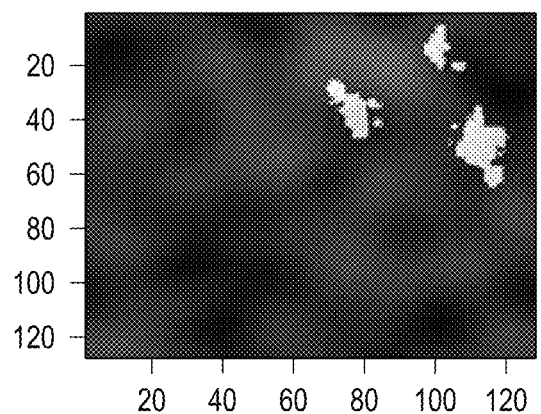
Figure 11B:
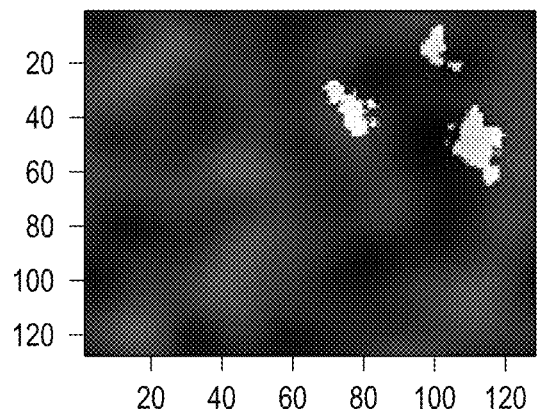
Figure 11B:
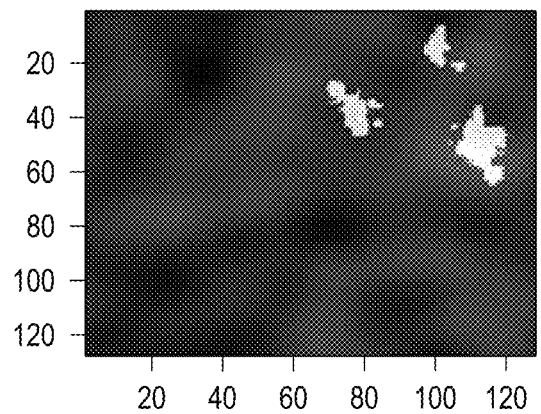

Synthetic models can be generated using mathematical computer models (e.g., as in FIGS. 6A-6B). For example, consider background that is generated synthetically, as shown in FIG. 10A. VICTRE was conducted in which computer-simulated synthetic DBT images were created and evaluated to detect lesions and calcifications and compared against synthetic DM images. The degree of uncertainty of evaluation in this trial was shown to be greater for detecting masses than it was for detecting calcifications, which provides evidence that synthetic images can be used to evaluate imaging devices. Assume, as shown in FIG. 10B, that there is a signal buried under the noise texture (here is a gaussian signal overlain on background of FIG. 10A). Note that the gaussian signal being observed is exaggerated in amplitude. FIG. 10C shows an example of a Laguerre basis function (a mathematical transform) for CHO analysis for mimicking eye behavior. This could be used to model the human eye model representing the pattern. L. Platisa, et al., "Channelized Hotelling observers for the assessment of volumetric imaging data sets," J. Opt. Soc. Am. A, Vol. 28(6), June 2011, which is incorporated by reference, describes the relevant CHO technology. FIG. 11A, in an alternate embodiment, shows a lumpy background that is generated synthetically, as shown in FIG. 10A. FIG. 11B shows calcifications superimposed upon the lumpy background of FIG. 11A.

Figure 12A:
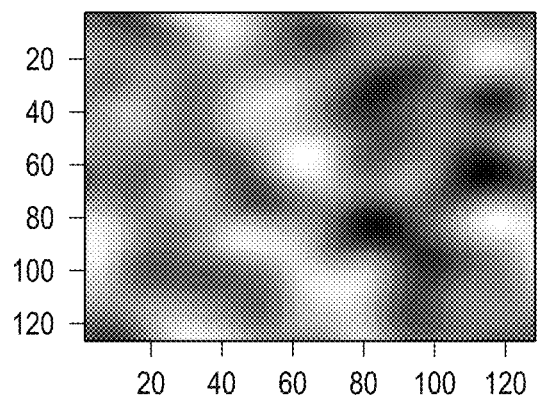
FIG. 12A shows image results of a synthetic run. The images of the phantom are shown with an ROC-like curve based on a CHO model.
Figure 12A:
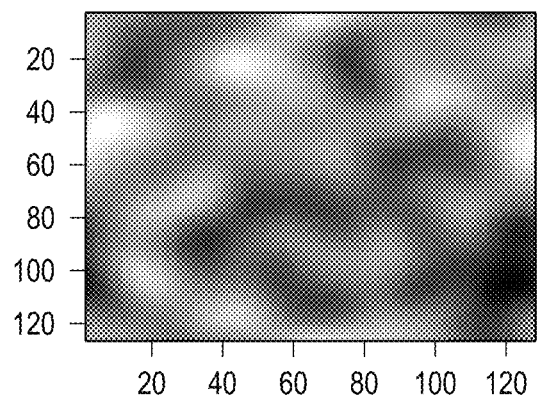
Figure 12A:
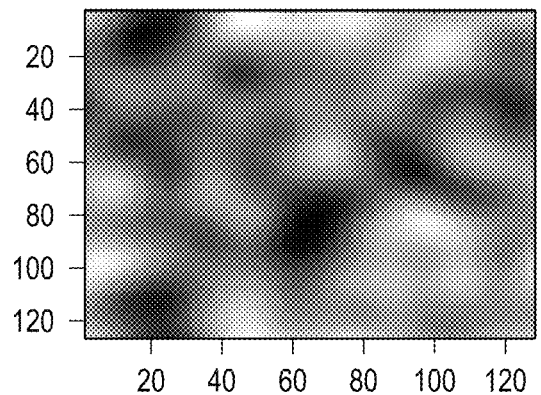
Figure 12A:
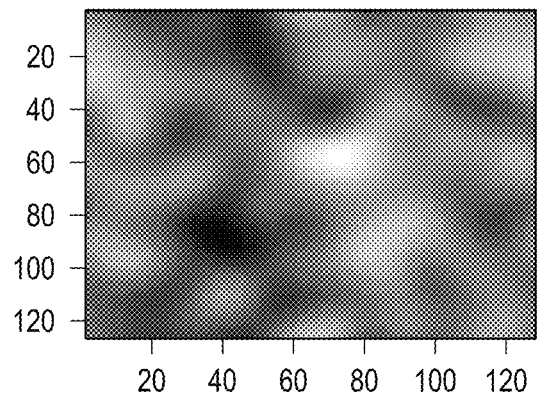
Figure 12B:
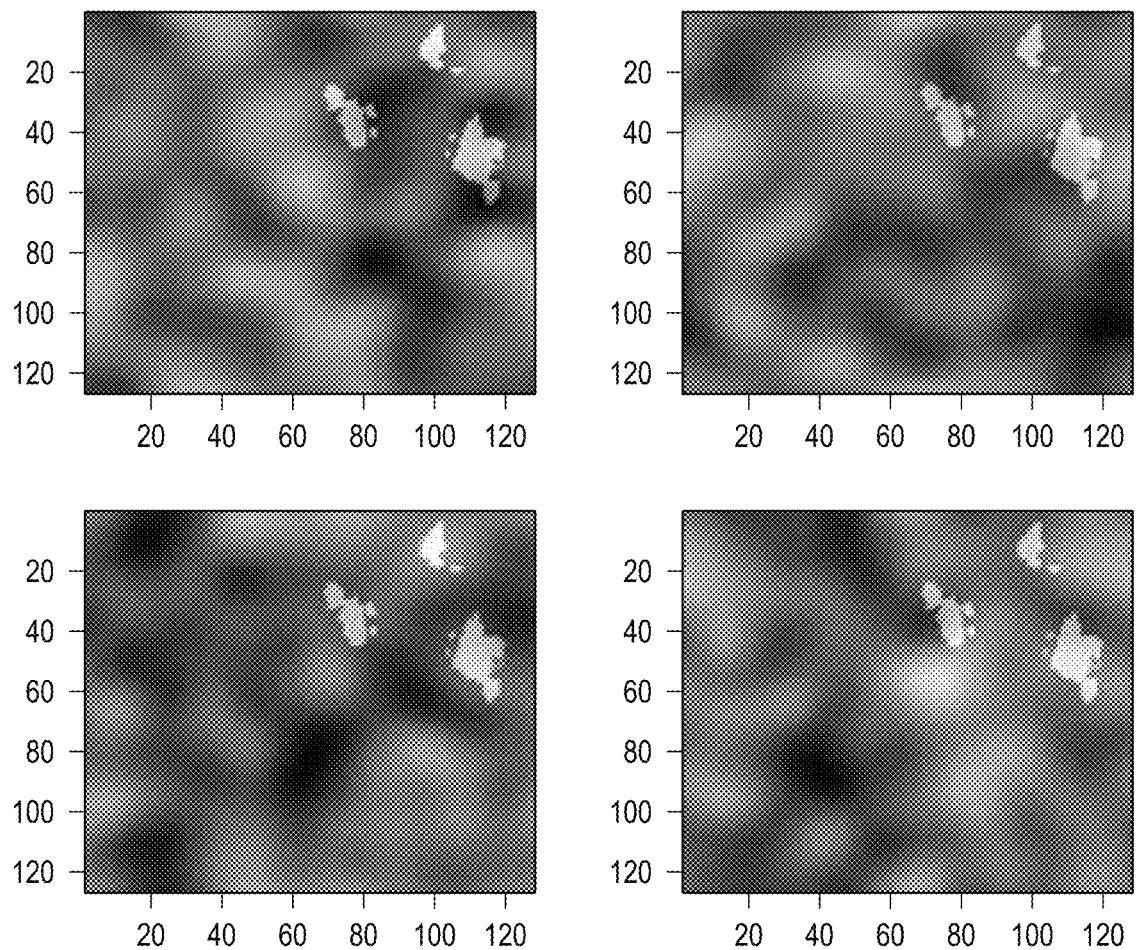
FIG. 12B shows a signal added from calcification images to the lumpy backgrounds of the images in FIG. 12A.
Figure 12C:
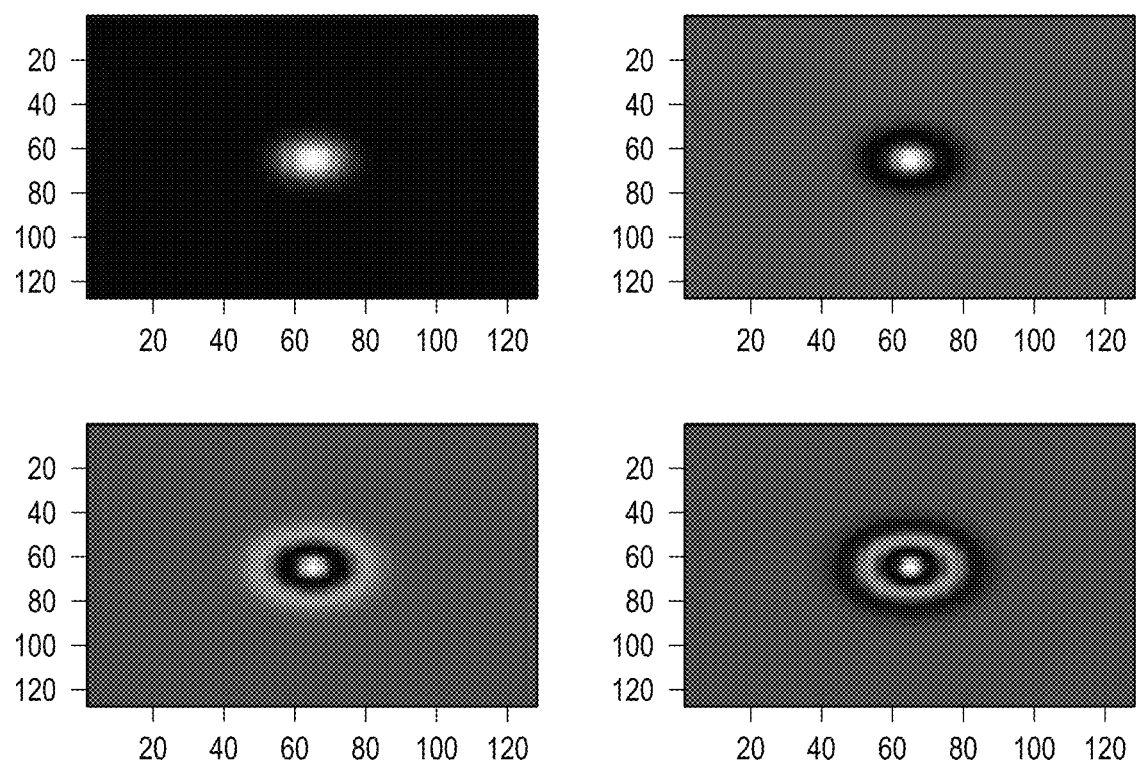
FIG. 12C shows examples of a Laguerre basis function for CHO analysis for mimicking eye behavior.
Figure 13A:
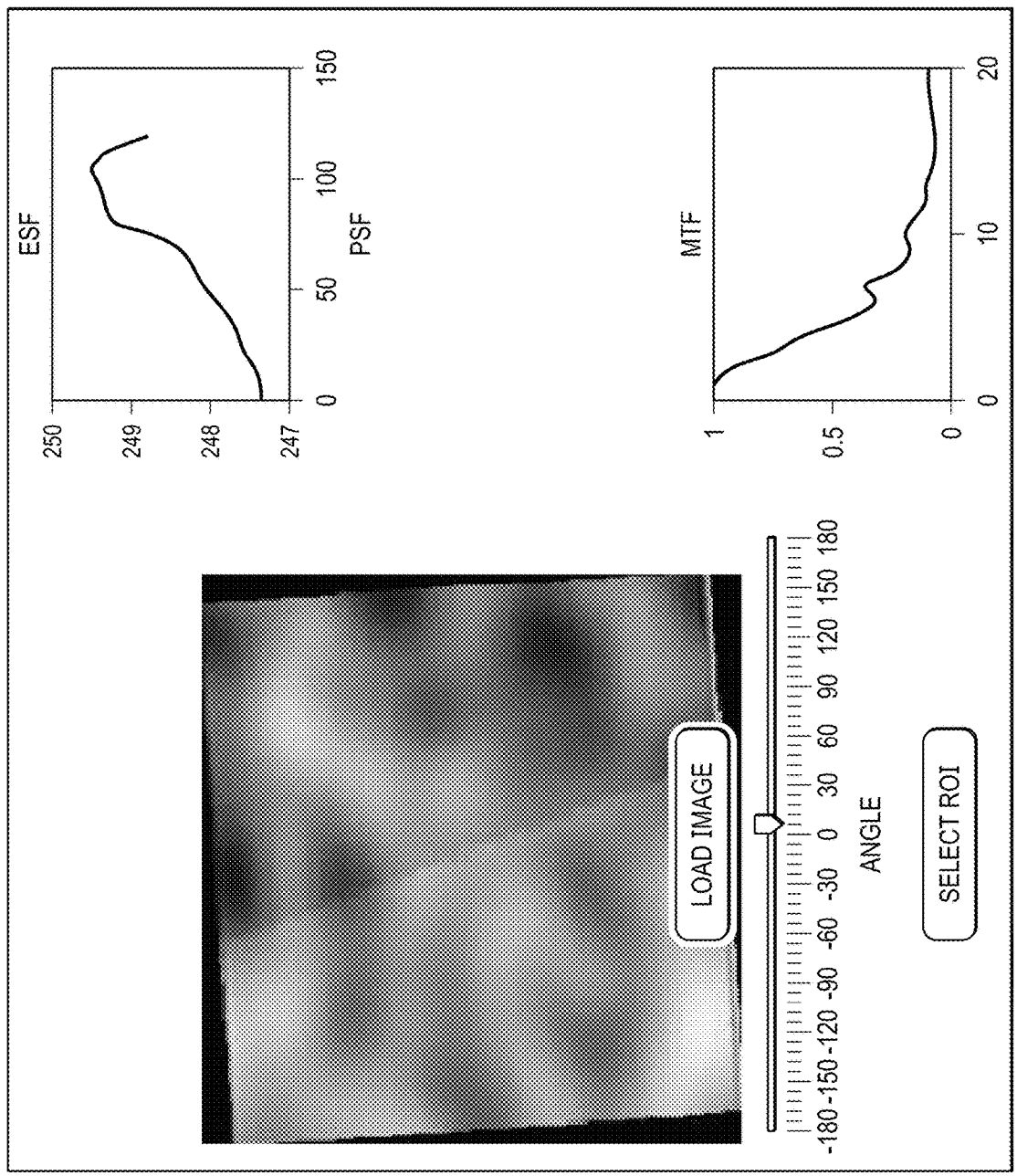
FIG. 13A shows ESF and MTF curves of a synthetically-generated lumpy background.
Figure 13B:
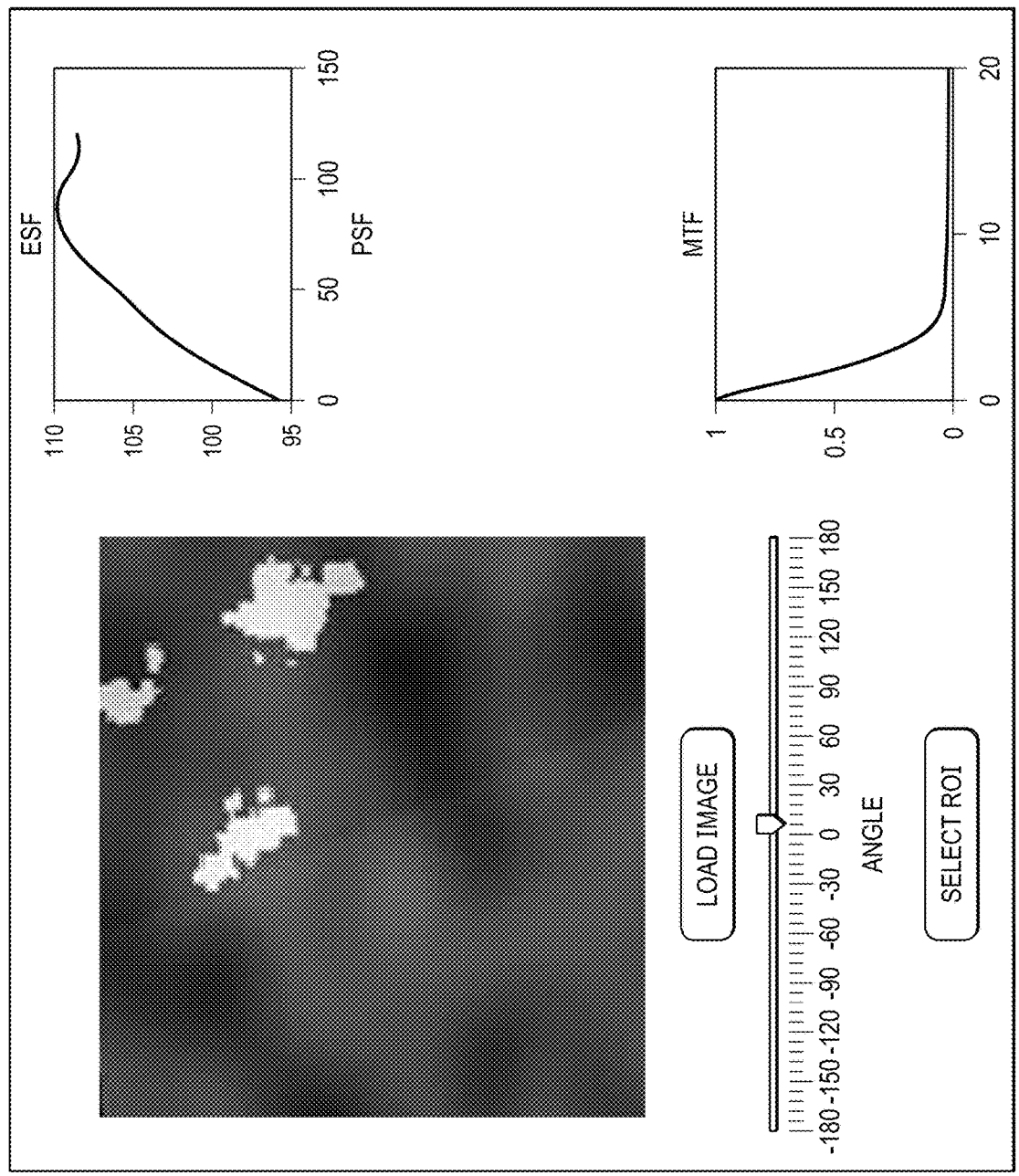
FIG. 13B shows ESF and MTF curves of a synthetically-generated lumpy background superimposed with calcification shapes, which can be used to characterize the performance of the image reconstruction, quality, and system performance of a phantom.

FIG. 12A shows image results of a synthetic run. The images of the phantom are shown with an ROC-like curve, based on a CHO model. FIG. 12B shows a signal added from calcification images to the lumpy background of the images in FIG. 12A. FIG. 12C shows examples of a Laguerre basis function for CHO analysis for mimicking eye behavior. FIG. 12D is a graph showing an ROC analysis as performed by the computer evaluation. Background can be constructed with the lumpy pattern density. FIG. 13A shows ESF and MTF curves of a synthetically-generated lumpy background. FIG. 13B shows ESF and MTF curves of a synthetically-generated lumpy background superimposed with calcification shapes, which can be used to characterize the performance of the image reconstruction, image quality, and system performance of a phantom.

Figure 15:
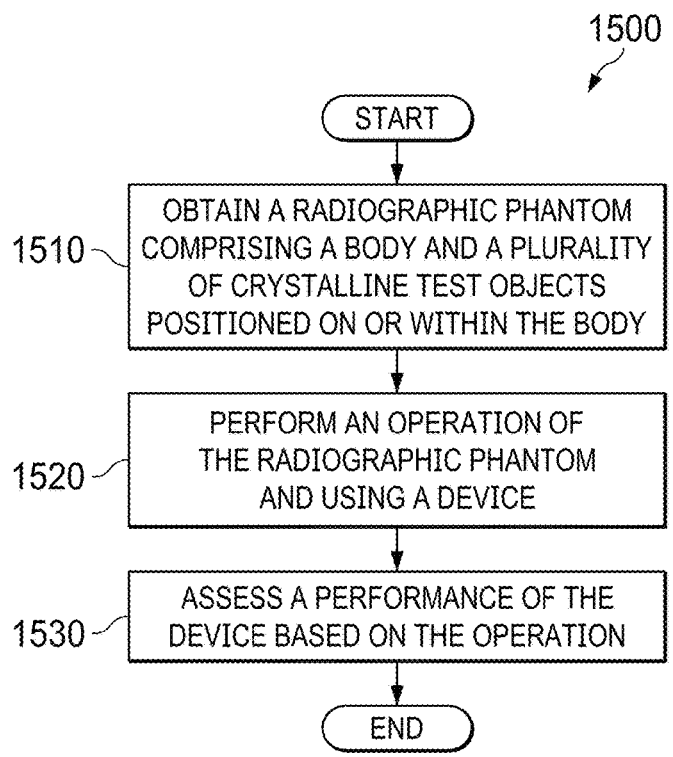
FIG. 15 is a flowchart illustrating a method of device performance assessment.

FIG. 15 is a flowchart illustrating a method 1500 of device performance assessment. At step 1510, a radiographic phantom comprising a body and a plurality of crystalline test objects positioned on or within the body is obtained. The body comprises a wax material or a wax-like material. The body has a density and an x-ray attenuation similar to that of a human breast tissue. At step 1520, an operation of the radiographic phantom and using a device is performed. At step 1530, a performance of the device is assessed based on the operation.

The method 1500 may implement additional embodiments as follows: The operation is a mammography operation. The method 1500 further comprises calibrating the device based on the performance. The method 1500 further comprises performing a selection of the crystalline test objects from a crystalline test object farm based on characteristics of the crystalline test objects, and positioning the crystalline test objects on or within the body. The selection is manual. The selection is at least partially automated using artificial intelligence. The method 1500 further comprises forming the crystalline test objects into channels of the body using microfluidics to model a desired pattern. The method further comprises obtaining a mathematical model for a desired radiographic phantom, and building the radiographic phantom according to the mathematical model.

Figure 16:
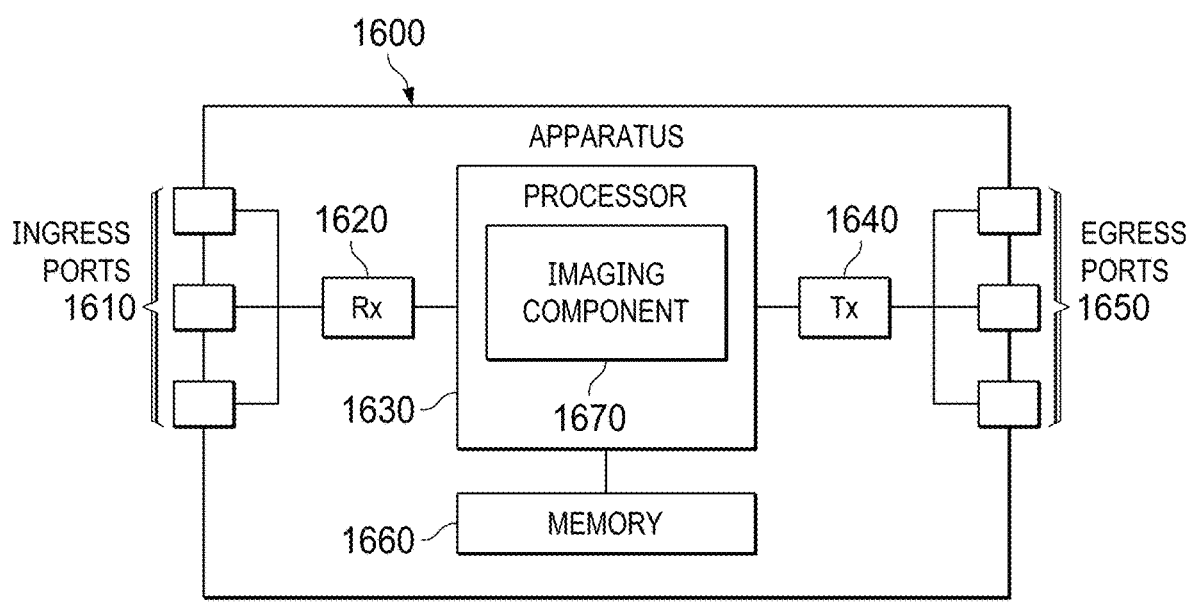
FIG. 16 is a schematic diagram of an apparatus according to an embodiment of the disclosure.

FIG. 16 is a schematic diagram of an apparatus 1600 according to an embodiment of the disclosure. The apparatus 1600 may implement the disclosed embodiments, for instance the robotics, AI, and image synthesis embodiments described above. The apparatus 1600 comprises ingress ports 1610 and an RX 1620 to receive data; a processor 1630, or logic unit, baseband unit, or CPU, to process the data; a TX 1640 and egress ports 1650 to transmit the data; and a memory 1660 to store the data. The apparatus 1600 may also comprise OE components, EO components, or RF components coupled to the ingress ports 1610, the RX 1620, the TX 1640, and the egress ports 1650 to provide ingress or egress of optical signals, electrical signals, or RF signals.

The processor 1630 is any combination of hardware, middleware, firmware, or software. The processor 1630 comprises any combination of one or more CPU chips, cores, FPGAs, ASICs, or DSPs. The processor 1630 communicates with the ingress ports 1610, the RX 1620, the TX 1640, the egress ports 1650, and the memory 1660. The processor 1630 comprises an imaging component 1670, which implements the disclosed embodiments. The inclusion of the imaging component 1670 therefore provides a substantial improvement to the functionality of the apparatus 1600 and effects a transformation of the apparatus 1600 to a different state. Alternatively, the memory 1660 stores the imaging component 1670 as instructions, and the processor 1630 executes those instructions.

The memory 1660 comprises any combination of disks, tape drives, or solid-state drives. The apparatus 1600 may use the memory 1660 as an over-flow data storage device to store programs when the apparatus 1600 selects those programs for execution and to store instructions and data that the apparatus 1600 reads during execution of those programs. The memory 1660 may be volatile or non-volatile and may be any combination of ROM, RAM, TCAM, or SRAM.

A computer program product may comprise computer-executable instructions that are stored on a non-transitory medium and that, when executed by a processor, cause an apparatus to perform any of the embodiments. The non-transitory medium may be the memory 1660, the processor may be the processor 1630, and the apparatus may be the apparatus 1600.

In at least one embodiment, the present disclosure is directed to a design process comprising: (1) generating a target pattern for calcification and creating an image of an appropriate size, (2) creating a lumpy synthetic pattern by a computer program, (3) adding to the system a model from an image of calcification, such as obtained from a photo or image of an actual calcification structure, and (4) performing a CHO analysis according to an algorithm. In a non-limiting embodiment, step (4) may be performed by first generating M 'random' samples, for example M=100, thereby generating background images (call this set NN). Next, a second set SS is created, wherein NN is added to a signal that is desired to be detected in the presence of that noise (SS=Signal+NN). Means for both samples mean(SS) and mean(NN) at each pixel voxel are calculated. A covariance matrix evaluation is performed from both sets. W ho=0.5*(K0+K1)^-1*delta [mean(SS), mean(NN)]. K0 is the covariance matrix of NN and K1 is the covariance matrix of SS. When/if uses the basis function (U) such as Laguerre (both Gabor channels or others can be used). This 'channelization' is meant to mimic the way the eye works mathematically. Next, W is multiplied by Ut*delta[mean(SS), mean(NN)] to obtain a set of test vectors after operating these on the SS and NN. The test vector results are sorted to create a set after sorting the values N, N, N, N, S, N, N, S, S, S, N, S . . . then one moves up the unique levels and considers values above a threshold that select S to be true positives, and the number N above that level as false positives. Then, TP rate and FP rate are returned and can be used to produce an ROC.-like curve.

As noted above, in at least certain embodiments, the phantoms have densities and X-ray attenuation values which approximate those of human breast tissues. In experiments, half-value layer (HVL) data of breast phantoms as described elsewhere herein was acquired using a Hologic Selenia Dimensions mammography system (Table 1). HVL is defined as the thickness of a phantom that is required to reduce the intensity of an X-ray beam to half of its initial value. For instance, at 30 kVp (peak kilovoltage) and W/Rh, the phantom material of 16.52 mm will reduce the X-ray intensity to half. This system has tomosynthesis (3D) capabilities. The target and filter combinations of the system include: Tungsten target with Rhodium filter (W/Rh), Tungsten target with Silver filter (W/Ag), and Tungsten target with Aluminum filter (W/Al). W/Rh and W/Ag are used for the 2D exposures, and W/Al is used for 3D (tomosynthesis) exposures. When kVp increases, the X-ray beam becomes more penetrating and thus need thicker phantom materials to attenuate the beam to half of its intensity. This is observed for all target and filter combinations. For instance, when kVp increases from 26 to 35 for W/Rh beam, the HVL increases from 15.85 mm to 17.22 mm. The wax phantom thickness will determine the attenuation of the X-ray beam. Because the wax phantom could be made at any thickness, e.g. 5 mm to 10 cm or more, the phantom can simulate any thickness of compressed breast. The typical thickness of a compressed breast is 4.5 cm.

TABLE 1

HVL of breast phantom for different kVp and Target/Filter combinations

| kVp | 26 | 27 | 28 | 29 | 30 | 31 | 32 | 33 | 34 | 35 |
|---|---|---|---|---|---|---|---|---|---|---|
| Wax HVL (W/Rh, mm) | 15.85 | 16.02 | 16.21 | 16.26 | 16.52 | 16.71 | 16.82 | 16.91 | 17.09 | 17.22 |
| Wax HVL (W/Ag, mm) | 16.43 | 16.76 | 17.05 | 17.30 | 17.55 | 17.75 | 17.96 | 18.22 | 18.41 | 18.62 |
| Wax HVL (W/Al, mm) | 14.45 | 14.91 | 15.30 | 15.59 | 15.94 | 16.37 | 16.71 | 17.02 | 17.27 | 17.55 |

In at least certain non-limiting embodiments, the present disclosure is directed to a radiographic phantom comprising a body comprising a wax material or a wax-like material, wherein the body has an x-ray attenuation value that is approximately the same as that of a human tissue; and a plurality of crystalline test objects positioned on or within the body. The human tissue may be a human breast tissue. In certain embodiments the human breast tissue may be a low-density fatty tissue or a high-density breast tissue. In certain embodiments, the human breast tissue has a density classification selected from the group consisting of Breast Imaging-Reporting and Data System (BI-RADS) Category 1, Category 2, Category 3, and Category 4. The body may comprise at least two layers of the wax material or the wax-like material, and wherein the plurality of crystalline test objects is positioned between the at least two layers. The plurality of crystalline test objects may be positioned along a straight line or a curved line upon or within the body. The plurality of crystalline test objects may be positioned on a fiber upon or within the body. The plurality of crystalline test objects may be positioned into channels within the body, the channels having a predetermined pattern. The plurality of crystalline test objects may comprise a salt selected from the group consisting of hydroxyapatite, calcium magnesium carbonate, calcium phosphate, calcium pyrophosphate, calcium sodium phosphate, calcium sodium pyrophosphate, calcium carbonate, calcium oxalate, calcium chloride, calcium oxide, sodium chloride, potassium chloride, barium chloride, potassium sulfate, sodium sulfide, aluminum oxide, and titanium oxide. The wax material or the wax-like material may be selected from the group consisting of a petroleum-derived waxy material (e.g., paraffin wax), an animal wax (e.g., a beeswax, a sealing wax, or a lanolin), a plant wax (e.g., a carnauba wax, a soy wax, a castor wax, or a tallow tree wax), and a polyethylene wax.

In at least certain non-limiting embodiments, the present disclosure is directed to a method comprising (1) obtaining a radiographic phantom comprising a body and a plurality of crystalline test objects positioned on or within the body, wherein the body comprises a wax material or a wax-like material, and wherein the body has an x-ray attenuation value that is approximately the same as that of a human breast tissue, (2) performing an operation of the radiographic phantom and using a device, and (3) assessing a performance of the device based on the operation. The operation may be a mammography operation. The method may comprise the step of calibrating the device based on the performance. The method may comprise the step of preselecting the plurality of crystalline test objects from a crystalline test object farm prior to being positioned on or within the body. The step of preselecting the plurality of crystalline test objects may have been performed manually. The step of preselecting the plurality of crystalline test objects may have been performed at least partially using artificial intelligence.

The plurality of crystalline test objects may be positioned into channels within the body, the channels having a predetermined pattern modeled by a microfluidics model. The method may comprise the steps of obtaining a mathematical model for a desired radiographic phantom configuration, and building the radiographic phantom according to the mathematical model for the desired radiographic phantom configuration. In certain embodiments of the method, the human breast tissue may be a low-density fatty tissue or a high density breast tissue. In certain embodiments, the human breast tissue has a density classification selected from the group consisting of Breast Imaging-Reporting and Data System (BI-RADS) Category 1, Category 2, Category 3, and Category 4. The body may comprise at least two layers of the wax material or the wax-like material, and wherein the plurality of crystalline test objects is positioned between the at least two layers. The plurality of crystalline test objects may be positioned along a straight line or a curved line upon or within the body. The plurality of crystalline test objects may be positioned on a fiber upon or within the body. The plurality of crystalline test objects may be positioned into channels within the body, the channels having a predetermined pattern. The plurality of crystalline test objects may comprise a salt selected from the group consisting of hydroxyapatite, calcium magnesium carbonate, calcium phosphate, calcium pyrophosphate, calcium sodium phosphate, calcium sodium pyrophosphate, calcium carbonate, calcium oxalate, calcium chloride, calcium oxide, sodium chloride, potassium chloride, barium chloride, potassium sulfate, sodium sulfide, aluminum oxide, and titanium oxide. The wax material or the wax-like material may be selected from the group consisting of a petroleum-derived waxy material (e.g., paraffin wax), an animal wax (e.g., a beeswax, a sealing wax, or a lanolin), a plant wax (e.g., a carnauba wax, a soy wax, a castor wax, or a tallow tree wax), and a polyethylene wax.

While the present disclosure has been described in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the presently disclosed methods and compositions. Changes may be made in the formulation of the various compositions described herein, the methods described herein or in the steps or the sequence of steps of the methods described herein without departing from the spirit and scope of the present disclosure.

What is claimed is:

1. A radiographic phantom comprising:
a body comprising a wax material or a wax-like material, wherein the body has an x-ray attenuation value that is approximately the same as that of a human tissue; and
a plurality of crystalline test objects positioned on or within the body, wherein the crystalline test objects comprise a salt selected from the group consisting of calcium phosphate, calcium pyrophosphate, calcium sodium phosphate, calcium sodium pyrophosphate, calcium oxalate, calcium chloride, calcium oxide, sodium chloride, potassium chloride, barium chloride, potassium sulfate, sodium sulfide, aluminum oxide, and titanium oxide.

2. The radiographic phantom of claim 1, wherein the human tissue is a breast tissue.

3. The radiographic phantom of claim 2, wherein the breast tissue is selected from a fatty, low-density breast tissue and a dense breast tissue.

4. The radiographic phantom of claim 1, wherein the body comprises at least two layers of the wax material or the wax-like material, and wherein the crystalline test objects are positioned between the at least two layers.

5. The radiographic phantom of claim 1, wherein the crystalline test objects are positioned within channels in the body.

6. The radiographic phantom of claim 1, wherein the crystalline test objects are positioned along a straight line or a curved line upon or within the body.

7. The radiographic phantom of claim 1, wherein the crystalline test objects are positioned on a fiber upon or within the body.

8. The radiographic phantom of claim 1, wherein the wax material or the wax-like material is selected from the group consisting of a petroleum-derived waxy material, an animal wax, a plant wax, and a polyethylene wax.

9. The radiographic phantom of claim 8, wherein the petroleum-derived waxy material is a paraffin wax.

10. The radiographic phantom of claim 8, wherein the animal wax is a beeswax, a sealing wax, or a lanolin.

11. The radiographic phantom of claim 8, wherein the plant wax is a carnauba wax, a soy wax, a castor wax, or a tallow tree wax.

12. The radiographic phantom of claim 1, wherein the crystalline test objects are of different shapes.

13. A method comprising:
obtaining a radiographic phantom comprising a body and a plurality of crystalline test objects, wherein the body comprises a wax material or a wax-like material, and wherein the body has an x-ray attenuation value that is approximately the same as that of a human breast tissue;
positioning the crystalline test objects within a pattern of channels in the body, wherein the pattern of channels is based on a microfluidics model;
performing an operation of the radiographic phantom and using a device; and
assessing a performance of the device based on the operation.

14. The method of claim 13, wherein the human breast tissue is selected from a fatty, low-density breast tissue and a dense breast tissue.

15. The method of claim 13, wherein the operation is a mammography operation.

16. The method of claim 13, further comprising the step of preselecting the plurality of crystalline test objects from a crystalline test object farm prior to the crystalline test objects being positioned on or within the body.

17. The method of claim 16, wherein the step of preselecting the plurality of crystalline test objects is performed manually, or at least partially using artificial intelligence.

18. The method of claim 13, further comprising growing the crystalline test objects in a crystal farm.

19. A method comprising:
obtaining a mathematical model for a desired radiographic phantom configuration; and
building a radiographic phantom according to the desired radiographic phantom configuration of the mathematical model, wherein the radiographic phantom comprises a body and a plurality of crystalline test objects positioned on or within the body, wherein the body comprises a wax material or a wax-like material, wherein the body has an x-ray attenuation value that is approximately the same as that of a human breast tissue, wherein the crystalline test objects are positioned within a pattern of channels in the body, and wherein the pattern of channels is based on a microfluidics model;
performing an operation of the radiographic phantom and using a device; and
assessing a performance of the device based on the operation.

20. The method of claim 19, further comprising growing the crystalline test objects in a crystal farm.

* * * * *